US012648943B2

(12) United States Patent
Greenstein et al.

(10) Patent No.: US 12,648,943 B2
(45) Date of Patent: Jun. 9, 2026

(54) TREATMENT OF ADRENOCORTICAL CARCINOMA WITH SELECTIVE GLUCOCORTICOID RECEPTOR MODULATORS (SGRMS) AND ANTIBODY CHECKPOINT INHIBITORS

(71) Applicant: Corcept Therapeutics Incorporated, Menlo Park, CA (US)

(72) Inventors: Andrew Greenstein, Menlo Park, CA (US); Andreas Grauer, Menlo Park, CA (US); Stacie Shepherd, Menlo Park, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 936 days.

(21) Appl. No.: 17/792,675

(22) PCT Filed: Jan. 26, 2021

(86) PCT No.: PCT/US2021/015124

§ 371 (c)(1),
(2) Date: Jul. 13, 2022

(87) PCT Pub. No.: WO2021/154750

PCT Pub. Date: Aug. 5, 2021

(65) Prior Publication Data

US 2023/0053364 A1 Feb. 23, 2023

Related U.S. Application Data

(60) Provisional application No. 63/125,630, filed on Dec. 15, 2020, provisional application No. 63/040,941, filed on Jun. 18, 2020, provisional application No. 62/967,517, filed on Jan. 29, 2020.

(51) Int. Cl.

| | |
|---|---|
| ***A61P 5/38*** | (2006.01) |
| ***A61K 31/337*** | (2006.01) |
| ***A61K 31/4745*** | (2006.01) |
| ***A61K 31/513*** | (2006.01) |
| ***A61K 31/7068*** | (2006.01) |
| ***A61K 33/243*** | (2019.01) |
| ***A61K 39/395*** | (2006.01) |
| ***A61P 35/00*** | (2006.01) |
| *A61K 39/00* | (2006.01) |

(52) U.S. Cl.

CPC ........ *A61K 31/4745* (2013.01); *A61K 31/337* (2013.01); *A61K 31/513* (2013.01); *A61K 31/7068* (2013.01); *A61K 33/243* (2019.01); *A61K 39/3955* (2013.01); *A61P 5/38* (2018.01); *A61P 35/00* (2018.01); *A61K 2039/505* (2013.01)

(58) Field of Classification Search

CPC .............. A61K 31/4745; A61K 31/337; A61K 31/513; A61K 31/7068; A61K 33/243; A61K 39/3955; A61K 2039/505; A61K 45/06; A61K 31/336; A61P 5/38; A61P 35/00; C07K 16/28; C07K 2317/76; C07K 2317/92

USPC .......................................................... 424/133.1

See application file for complete search history.

(56) References Cited

U.S. PATENT DOCUMENTS

| | | | | |
|---|---|---|---|---|
| 7,678,813 | B2 | 3/2010 | Clark et al. | |
| 7,928,237 | B2 | 4/2011 | Clark et al. | |
| 8,461,172 | B2 | 6/2013 | Clark et al. | |
| 8,859,774 | B2 | 10/2014 | Hunt et al. | |
| 9,149,485 | B2 | 10/2015 | Pan et al. | |
| 10,047,082 | B2 | 8/2018 | Hunt et al. | |
| 10,980,797 | B2 * | 4/2021 | Hunt | C07K 16/2818 |
| 12,171,760 | B2 | 12/2024 | Hunt | |
| 2012/0238549 | A1 | 9/2012 | Cusack et al. | |
| 2014/0341849 | A1 | 11/2014 | Pan et al. | |

(Continued)

FOREIGN PATENT DOCUMENTS

| | | |
|---|---|---|
| CL | 2014003173 | 2/2015 |
| CN | 103957920 | 7/2014 |

(Continued)

OTHER PUBLICATIONS

Lu et al., "Combined Pd-1 Blockade and Gitr Triggering Induce a Potent Antitumor Immunity in Murine Cancer Models and Synergizes With Chemotherapeutic Drugs", Journal of Translational Medicine, vol. 12, No. 36, Feb. 7, 2014, pp. 1-11.

U.S. Appl. No. 17/210,245 , "Non-Final Office Action", May 11, 2023, 10 pages.

Hartkopf et al., "PD-1 and PD-L1 Immune Checkpoint Blockade to Treat Breast Cancer", Breast Care, vol. 11, Dec. 8, 2016, pp. 385-390.

Tacon et al., "The Glucocorticoid Receptor Is Overexpressed in Malignant Adrenocortical Tumors", The Journal of Clinical Endocrinology & Metabolism, vol. 94, No. 11, Nov. 30, 2009, pp. 4591-4599.

Israeli Patent Application No. 297201, "Office Action", Jun. 11, 2025, 3 pages.

(Continued)

*Primary Examiner* — Yan Xiao

(74) *Attorney, Agent, or Firm* — James Fox; Kilpatrick Townsend & Stockton LLP

(57) ABSTRACT

Methods and compositions for treating a subject suffering from adrenocortical carcinoma and having excess cortisol are disclosed. The methods provide therapeutic benefits including reduction of ACC tumor load, restoration of T-cell and natural killer (NK) cell signaling pathways, increase in T-cell and NK cell infiltration into the ACC tumor, reduction of neutrophil infiltration into the ACC tumor in the patient, and other therapeutic benefits. The methods include administration of a glucocorticoid receptor modulator (GRM) (which may be a selective glucocorticoid receptor modulator (SGRM)) and an antibody checkpoint inhibitor. In embodiments, the GRM (e.g., a SGRM) is orally administered. The GRM may be a nonsteroidal compound comprising: a fused azadecalin structure; a heteroaryl ketone fused azadecalin structure; or an octahydro fused azadecalin structure.

7 Claims, 16 Drawing Sheets

(56) References Cited

U.S. PATENT DOCUMENTS

| | | | |
|---|---|---|---|
| 2015/0080389 A1 | 3/2015 | Hunt et al. |
| 2015/0118244 A1 | 4/2015 | Shahabi et al. |
| 2015/0346210 A1 | 12/2015 | Nitta et al. |
| 2018/0064679 A1 | 3/2018 | Pierce et al. |
| 2019/0083486 A1 | 3/2019 | Hunt |

FOREIGN PATENT DOCUMENTS

| | | |
|---|---|---|
| CN | 104619328 | 5/2015 |
| JP | 2014530812 | 11/2014 |
| JP | 2015517580 | 6/2015 |
| JP | 2018503663 A | 2/2018 |
| WO | 2013039916 | 3/2013 |
| WO | 2013052652 | 4/2013 |
| WO | 2013177559 | 11/2013 |
| WO | 2014039461 A1 | 3/2014 |
| WO | 2014197470 A1 | 12/2014 |
| WO | 2015037000 A1 | 3/2015 |
| WO | 2015061752 | 4/2015 |
| WO | 2015070060 | 5/2015 |
| WO | 2015077414 | 5/2015 |
| WO | 2015077530 | 5/2015 |
| WO | 2015095811 | 6/2015 |
| WO | 2015100282 | 7/2015 |
| WO | 2017151613 | 9/2017 |
| WO | 2018195450 A1 | 10/2018 |
| WO | 2021076565 A1 | 4/2021 |

OTHER PUBLICATIONS

Korean Patent Application No. 10-2018-7027525, "Notice of Decision to Grant", Jul. 4, 2025, 3 pages.
Singaporean Patent Application No. 11202251413A , "Written Opinion", Sep. 11, 2024, 11 pages.
Anonymous, "Study of Relacorilant in Combination With Pembrolizumab for Patients With Adrenocortical Carcinoma Which Produces Too Much Stress Hormone (Cortisol)", Available online at: https://classic.clinicaltrials.gov/ct2/show/NCT04373265, May 4, 2020, 9 pages.
European Patent Application No. 21747777.7 , "Extended European Search Report", Sep. 26, 2023, 12 pages.
Habra et al., "Phase II Clinical Trial of Pembrolizumab Efficacy and Safety in Advanced Adrenocortical Carcinoma", Journal for Immunotherapy of Cancer, vol. 7, No. 1, Sep. 18, 2019, pp. 1-9.
Peppa et al., "Adrenocortical Carcinoma Secreting Cortisol, Androgens and Aldosterone: a Case Report", Biomed Central Ltd, vol. 2, No. 1, Sep. 10, 2009, pp. 1-4.
Abiven et al., "Clinical and Biological Features in the Prognosis of Adrenocortical Cancer: Poor Outcome of CortisolSecreting Tumors in a Series of 202 Consecutive Patients", The Journal of Clinical Endocrinology & Metabolism, vol. 91, No. 7, Jul. 2006, pp. 2650-2655.
Japanese Patent Application No. 2022-546570 , "Office Action", Oct. 17, 2023, 8 pages.
"American Society of Clinical Oncology Annual Meeting", Clinical Care Options, Oncology, Available Online at https://www.clinicaloptions.com/oncology/conference-coverage/clin-onc-june-2015/immunotherapy/Iba100, Jun. 2, 2015, 9 pages.
"Sygnature Discovery Delivers Clinical Candidate to Corcept Therapeutics", Sygnature Discovery, Jul. 30, 2015, 6 pages.
Clark et al., "2-Benzenesulfonyl-8a-Benzyl-Hexahydro-2h-Isoquinolin-6-ones as Selective Glucocorticoid Receptor Antagonists", Bioorganic & Medicinal Chemistry Letters, vol. 17, No. 20, Oct. 15, 2007, pp. 5704-5708.
Goyeneche et al., "Mifepristone Inhibits Ovarian Cancer Cell Growth in Vitro and in Vivo", Clinical Cancer Research, vol. 11, No. 13, Jun. 1, 2007, pp. 3370-3379.
Hinrichs et al., "Glucocorticoids Do Not Inhibit Antitumor Activity of Activated CD8+ T Cells", Journal of Immunotherapy, vol. 28, No. 6, 2005, 17 pages.
Hunt et al., "Identification of the Clinical Candidate (R)-(1-(4-Fluorophenyl)-6-((1-Methyl-1H-Pyrazol-4-yl)Sulfonyl)-4,4a, 5,6, 7,8-Hexahydro-1H-Pyrazolo[3,4-g]lsoquinolin-4a-yl)(4-(Trifluoromethyl)Pyridin-2-yl)Methanone (CORT125134): A Selective Glucocorticoid Receptor", Journal of Medicinal Chemistry, vol. 60, No. 8, Apr. 27, 2017, pp. 3405-3421.
Iams et al., "PD-1 Inhibition and PD-1 Inhibitors", My Cancer Genome, Nov. 24, 2015, 5 pages.
Lee et al., "A New Addition to the PD-1 Checkpoint Inhibitors for Non-Small Cell Lung Cancer—The Anti-PDL1 Antibody-MEDI4736", Translational Lung Cancer Research, vol. 3, No. 6, Dec. 2014, pp. 408-410.
Lehmann et al., "The Molecular Basis of Adrenocortical Cancer", Cancer Genetics, vol. 205, Issue 4, Apr. 1, 2012, pp. 131-137.
Nocentini et al., "A New Member of the Tumor Necrosis Factorynerve Growth Factor Receptor Family Inhibits T Cell Receptor-Induced Apoptosis", Proc. Natl. Acad. Sci., vol. 94, Jun. 1997, pp. 6216-6221.
Application No. PCT/US2021/015124 , International Preliminary Report on Patentability, Mailed on May 20, 2022, 7 pages.
Application No. PCT/US2021/015124 , International Search Report and Written Opinion, Mailed on May 26, 2021, 12 pages.
Application No. PCT/US2021/015124 , Written Opinion of the International Preliminary Examining, Mailed on Mar. 21, 2022, 5 pages.
Peng et al., "Glucocorticoid Receptors in Hepatocellular Carcinoma and Adjacent Liver Tissue", Cancer, vol. 62, No. 10, Nov. 15, 1988, pp. 2134-2138.
Ramsay , "Immune Checkpoint Blockade Immunotherapy to Activate Anti-Tumour T-Cell Immunity", British Journal of Haematology, vol. 162, No. 3, Aug. 2013, pp. 313-325.
Schlossmacher et al., "Glucocorticoid Receptor-Mediated Apoptosis: Mechanisms of Resistance in Cancer Cells", Journal of Endocrinology, vol. 211, No. 1, Oct. 2011, pp. 17-25.
Skor et al., "Glucocorticoid Receptor Antagonism as a Novel Therapy for Triple-Negative Breast Cancer", Clinical Cancer Research, vol. 19, No. 22, Nov. 15, 2013, pp. 6163-6172.
Tacon et al., "The Glucocorticoid Receptor Is Overexpressed in Malignant Adrenocortical Tumors", The Journal of Clinical Endocrinology & Metabolism, vol. 94, Issue 11 Available Online at: https://doi.org/10.1210/jc.2009-0546, Nov. 1, 2009, pp. 4591-4599.
White, "Sygnature Discovery Delivers Clinical Candidate CORT125134 to Corcept", Sygnature Discovery News, https://www.drugtargetreview.com/news/5589/sygnature-discovery-delivers-clinical-candidate-cort125134-to-concept/, Jul. 30, 2015, pp. 1-2.

* cited by examiner

NK Cells

| | | | | |
|---|---|---|---|---|
| 500 U/ml IL-2 | - | + | + | + |
| 200 nM cortisol | - | - | + | + |
| 300 nM relacorilant | - | - | - | + |

| | | | | | |
|---|---|---|---|---|---|
| 500 U/ml IL-2 | - | + | + | + | + |
| 200 nM cortisol | - | - | + | - | + |
| 300 nM relacorilant | - | - | - | + | + |

TREATMENT OF ADRENOCORTICAL CARCINOMA WITH SELECTIVE GLUCOCORTICOID RECEPTOR MODULATORS (SGRMS) AND ANTIBODY CHECKPOINT INHIBITORS

CROSS-REFERENCE TO RELATED APPLICATIONS

This application is a 371 U.S. National Phase of PCT International Patent Application No. PCT/US2021/015124, filed on Jan. 26, 2021, which claims benefit and priority to U.S. provisional patent application Nos. 62/967,517, filed on Jan. 29, 2020, and 63/040,941, filed Jun. 18, 2020, and 63/125,630, filed Dec. 15, 2020. These references are incorporated by reference herein in their entirety for all purposes.

BACKGROUND

The adrenal glands are the natural source of the glucocorticoid (GC) cortisol. Cortisol is produced and secreted by the adrenal glands in response to adrenocorticotrophic hormone (ACTH) which is secreted by the pituitary gland. Cortisol levels vary during the course of the day and night, and may be measured in blood (e.g., serum, plasm, or whole blood) and may be measured in the morning (when cortisol levels are typically the highest). Cortisol levels may also be measured in urine (e.g., 24-hour urinary cortisol measurement, which may provide a cortisol measurement less affected by the time of day at which sampling was performed), saliva (e.g., late-night salivary cortisol, when the cortisol levels are typically lowest), and other bodily fluids (e.g., tears and sweat). Cortisol may also be measured after a dexamethasone suppression test, in which cortisol provides a measure of the response of the hypothalamic-pituitary-adrenal axis to externally administered glucocorticoids such as dexamethasone.

Elevated glucocorticoid (GC) activity, e.g. "cortisol excess" or "excess cortisol", while difficult to accurately quantify, has been implicated in the pathophysiology of multiple cancer types. Approximately half of adrenocortical carcinoma (ACC) patients exhibit overt clinical and biochemical evidence of systemic excess GC (GC+), which provides a unique test case to assess correlates of GC activity. The broad immunosuppressive effects of GC may limit tumor immune response and immune checkpoint inhibitor (ICI) efficacy.

Efficacy of antibody checkpoint inhibitors is limited in adrenocortical carcinoma (ACC). Approximately half of ACC patients have systemic cortisol excess (GC+). Excess cortisol causes Cushing's syndrome and other disorders. In addition, cortisol has immunosuppressive effects. Immune suppression is associated with poor response to checkpoint inhibitors. The specific immunosuppressive effects of cortisol in ACC are not known. Thus, the immune effects of an SGRM in GC+ ACC is not known.

There is need in the art to provide more effective treatments for ACC, including need to enhance the effects of antibody checkpoint inhibitor treatments for patients suffering from ACC.

SUMMARY

Adrenocortical carcinoma (ACC) multi-omics were analyzed to identify the molecular consequences of glucocorticoid (GC) activity and assess the rationale for combining relacorilant, a glucocorticoid receptor (GR) antagonist, with an immune checkpoint inhibitor (ICI) in adrenocortical carcinoma with glucocorticoid excess (GC+ ACC). Applicant analyzed publicly-available data on ACC tumor gene transcription and GC excess (e.g., excess cortisol).

Treatment methods include administration of a selective glucocorticoid receptor modulator (SGRM) and an antibody checkpoint inhibitor to a patient suffering from an adrenocortical carcinoma (ACC) and having cortisol excess. A patient has cortisol excess where that patient's cortisol levels exceed the normal range, e.g., are above the upper limit of normal cortisol. In embodiments, cortisol excess is identified where the patient's cortisol levels are equal to or greater than about one and one half (1.5) times the normal cortisol level, or are equal to or greater than about twice (2) times the normal cortisol level. In embodiments, cortisol excess is identified where atypical elevations are observed in a patient's diurnal cortisol rhythm.

Effects of cortisol excess may include, for example, increased cortisol effects on immune responses in and to the tumor (e.g., immune suppression in the tumor, lymph nodes, and elsewhere). In embodiments, administration of a SGRM in combination with an antibody checkpoint inhibitor may be effective to reduce or reverse the effects of cortisol excess in an ACC patient with cortisol excess, and may be effective to reduce ACC tumor load in the patient. In embodiments, administration of a SGRM in combination with an antibody checkpoint inhibitor may be effective to reduce or reverse the effects of cortisol excess in an ACC patient with cortisol excess, and may be effective to restore T-cell and natural killer (NK) cell signaling pathways in the patient. In embodiments, administration of a SGRM in combination with an antibody checkpoint inhibitor may be effective to reduce or reverse the effects of cortisol excess in an ACC patient with cortisol excess, and may be effective to increase T-cell and natural killer (NK) cell infiltration into the ACC tumor in the patient. In embodiments, administration of a SGRM in combination with an antibody checkpoint inhibitor may be effective to reduce or reverse the effects of cortisol excess in an ACC patient with cortisol excess, and may be effective to reduce neutrophil infiltration into the ACC tumor in the patient.

In some cases, the GRM (e.g., a SGRM) is a nonsteroidal compound comprising a fused azadecalin structure, wherein the fused azadecalin structure is as described and disclosed in U.S. Pat. No. 7,928,237 and in U.S. Pat. No. 8,461,172, the entire contents of both of which patents are hereby incorporated by reference in their entireties.

In some cases, the GRM (e.g., a SGRM) is a nonsteroidal compound comprising a heteroaryl ketone fused azadecalin structure, wherein the heteroaryl ketone fused azadecalin structure is as described and disclosed in U.S. Pat. No. 8,859,774, the entire contents of which is hereby incorporated by reference in its entirety.

In some cases, the GRM (e.g., a SGRM) is a nonsteroidal compound comprising an octahydro fused azadecalin structure, wherein the octahydro fused azadecalin structure is as described and disclosed in U.S. Pat. No. 10,047,082, the entire contents of which is hereby incorporated by reference in its entirety.

In some cases, the GRM (e.g., a SGRM, such as a nonsteroidal SGRM) is orally administered.

The present methods provide improved methods of treating adrenocortical carcinoma (ACC). The methods disclosed herein are believed to provide therapeutic benefits to patients suffering from ACC, where such therapeutic benefits include, for example, reduction ACC tumor load; restoration of T-cell and natural killer (NK) cell signaling pathways;

increase in T-cell and NK cell infiltration into the ACC tumor; reduction of neutrophil infiltration into the ACC tumor in the patient; and other therapeutic benefits.

DETAILED DESCRIPTION

A. Introduction

Figure 1:
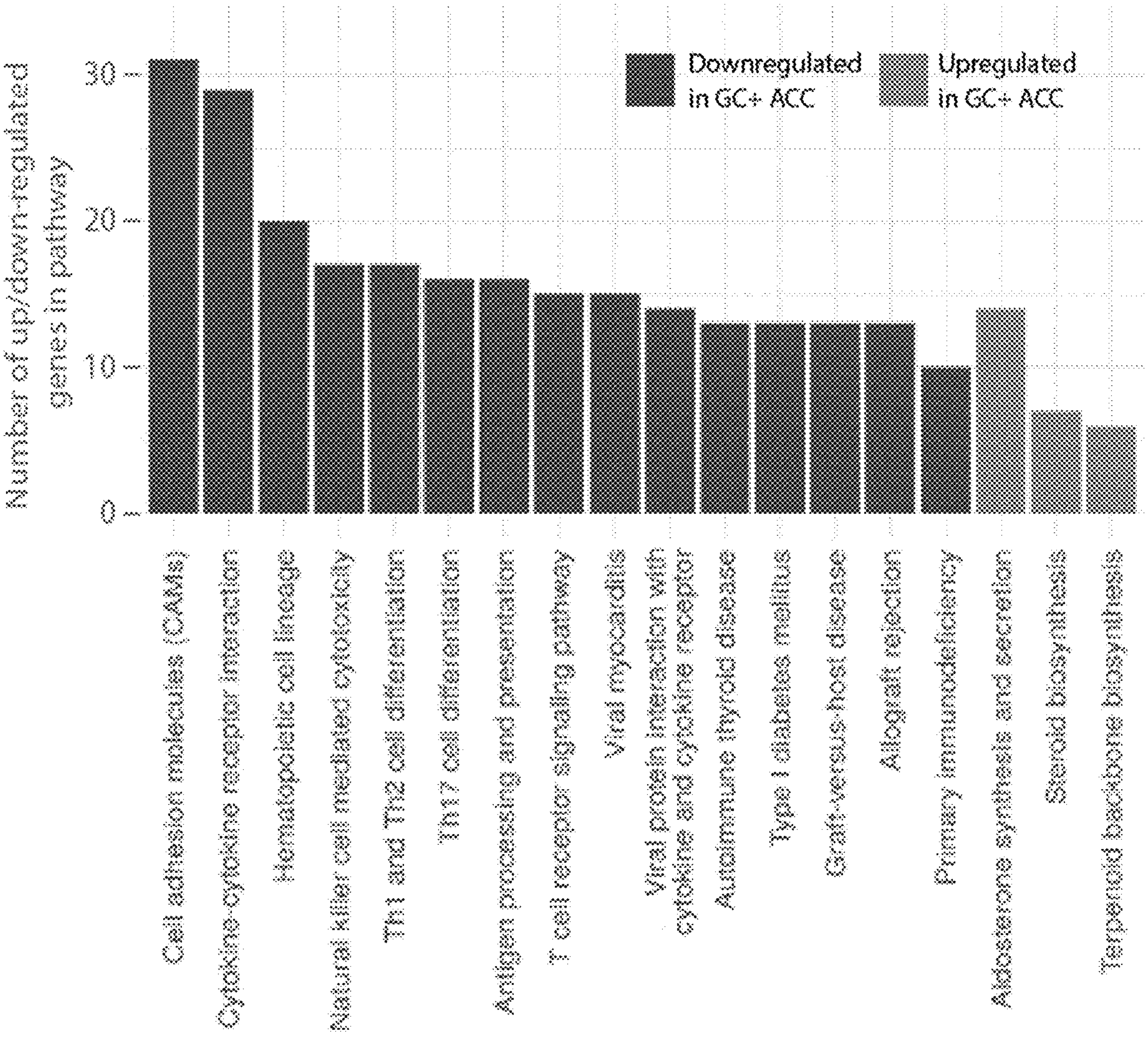
FIG. 1 shows differences in transcriptional pathways in GC+ ACC cases ("GC+" indicates ACC patients exhibiting GC excess). Downregulation refers to pathways lower in GC+ ACC cases, while upregulation refers to pathways elevated in GC+ ACC.

Applicant analyzed adrenocortical carcinoma (ACC) tumor gene transcription; the data was screened to identify such gene transcription in ACC patients with, and ACC patients without, glucocorticoid (GC) excess (e.g., excess cortisol). Applicant has discovered that cortisol excess alters the expression of 858 genes in adrenocortical carcinoma (ACC). Specifically, genes involved in natural killer (NK) mediated cytotoxicity, $T_H17$ cell differentiation, T cell receptor signaling, $T_H1/2$ differentiation, and antigen processing and presentation were downregulated in ACC tumors in patients having cortisol excess (GC+; see FIG. 1). Further differences are also shown in FIG. 1 and elsewhere herein.

Applicant has also discovered that the presence of specific immune cells was different in ACC tumors with or without cortisol excess. Naïve and memory CD4+ cells, CD8+ cells, CD8+ central memory cells, and natural killer T-cells (NKT)s were lower in GC+ cases (see FIG. 2). In contrast, tumor associated neutrophils (TAN) were higher in ACC patients with GC+.

A patient's clinical response to antibody checkpoint inhibitors is dependent on the immune system. Specifically, T-cell function and antigen presentation are critical for clinical efficacy of antibody checkpoint inhibitors. Further, infiltration of immune cells into a tumor is associated with clinical efficacy of antibody checkpoint inhibitors. Tumors with low T-cell cell numbers or with high neutrophil infiltration tend to have poor responses to antibody checkpoint inhibitors.

Applicant discloses herein that administration an antibody checkpoint inhibitor along with administration of a SGRM, where the SGRM administration is effective to reduce or reverse the effects of cortisol excess in an ACC patient with cortisol excess, may improve that patient's response to administration of an antibody checkpoint inhibitor, thereby improving the treatment of the ACC patient with cortisol excess. In embodiments, administration of a SGRM in combination with an antibody checkpoint inhibitor may be effective to reduce or reverse the effects of cortisol excess in an ACC patient with cortisol excess, and may be effective to reduce ACC tumor load in the patient.

Applicant further discloses herein that administration of an antibody checkpoint inhibitor along with administration of a SGRM, where the SGRM administration is effective to restore T-cell and NK cell signaling pathways in the patient (including in an ACC tumor of that patient). Such restoration of T-cell and NK cell signaling pathways may improve that patient's response to administration of an antibody checkpoint inhibitor, and thus improve the treatment of the ACC patient with cortisol excess. In embodiments, administration of a SGRM, effective to restore T-cell and NK cell signaling pathways in the patient (including in an ACC tumor of that patient), may be effective to reduce ACC tumor load in the patient.

Applicant further discloses herein that administration an antibody checkpoint inhibitor along with administration of a SGRM, where the SGRM administration is effective to increase T-cell and NK cell infiltration into an ACC tumor in the patient. Such increased T-cell and NK cell infiltration may improve that patient's response to administration of an antibody checkpoint inhibitor, and thus improve the treatment of the ACC patient with cortisol excess. In embodiments, administration of a SGRM, effective to increase T-cell and NK cell infiltration into an ACC tumor in the patient may be effective to reduce ACC tumor load in the patient.

Applicant further discloses herein that administration an antibody checkpoint inhibitor along with administration of a SGRM, where the SGRM administration is effective to decrease neutrophil infiltration into an ACC tumor in the patient. Such decreased neutrophil infiltration may improve that patient's response to administration of an antibody checkpoint inhibitor, and thus improve the treatment of the ACC patient with cortisol excess. In embodiments, administration of a SGRM, effective to decrease neutrophil infiltration into an ACC tumor in the patient may be effective to reduce ACC tumor load in the patient.

B. Definitions

The term "about" when used in reference to a pre-determined value denotes a range encompassing plus or minus 10% of the pre-determined value.

Information regarding cancers is found, for example, in The Cancer Genome Atlas (TGCA). Access to TGCA is found via the National Cancer Institute web-site (www.cancer.gov) at the "about-nci/organization/ccg/research/structural-genomics/tcga" page. The following abbreviations are used herein to refer to different types of cancer:

| | |
|---|---|
| ACC | Adrenocortical carcinoma |
| BLCA | Bladder Urothelial Carcinoma |
| BRCA | Breast invasive carcinoma |
| CESC | Cervical squamous cell carcinoma and endocervical adenocarcinoma |
| CHOL | Cholangiocarcinoma |
| LIHC | Liver hepatocellular carcinoma |
| LUAD | Lung adenocarcinoma |
| LGG | Low grade glioma |
| LUSC | Lung squamous cell carcinoma |
| OV | Ovarian serous cystadenocarcinoma |
| PAAD | Pancreatic adenocarcinoma |
| PRAD | Prostate adenocarcinoma |
| SKCM | Skin Cutaneous Melanoma |
| UVM | Uveal Melanoma |

As used herein, the term "tumor" and the term "cancer" are used interchangeably and both refer to an abnormal growth of tissue that results from excessive cell division. A tumor that invades the surrounding tissue and/or can metastasize is referred to as "malignant." A tumor that does not metastasize is referred to as "benign."

As used herein, the term "adrenocortical carcinoma" and the acronym "ACC" are used interchangeably to refer to adrenal gland adrenocarcinomas.

As used herein, the term "natural killer cell" and the abbreviations "NK cell", "NKT-cell", and the like, including their plural forms, are used as known in the art, to refer to cytotoxic lymphocytes of the immune system.

As used herein, the term "T-cell" is used, as known in the art, to refer to thymus-derived lymphocytes that play important roles in the immune response.

As used herein, the term "neutrophil" is used, as known in the art, to refer to the most abundant type of white blood cell, and which are the most abundant type of granulocytes, in mammals. Neutrophils are also sometimes referred to as "neutrocytes".

As used herein, the term "infiltration" refers to invasion and occupation of a tissue (such as an ACC tumor) by cells that originated in a distinct tissue, such as T-cells, NK cells, or neutrophils.

As used herein, the term "patient" refers to a human that is or will be receiving, or has received, medical care for a disease or condition.

As used herein, the terms "administer," "administering," "administered" or "administration" refer to providing a compound or a composition (e.g., one described herein), to a subject or patient. For example, a compound or composition may be administered orally to a patient.

As used herein, the terms "administer," "administering," "administered" or "administration" refer to providing a compound or a composition (e.g., one described herein), to a subject or patient. Administration may be by oral administration (i.e., the subject receives the compound or composition via the mouth, as a pill, capsule, liquid, or in other form suitable for administration via the mouth. Oral administration may be buccal (where the compound or composition is held in the mouth, e.g., under the tongue, and absorbed there). Administration may be by injection, i.e., delivery of the compound or composition via a needle, microneedle, pressure injector, or other means of puncturing the skin or forcefully passing the compound or composition through the skin of the subject. Injection may be intravenous (i.e., into a vein); intraarterial (i.e., into an artery); intraperitoneal (i.e., into the peritoneum); intramuscular (i.e., into a muscle); or by other route of injection. Routes of administration may also include rectal, vaginal, transdermal, via the lungs (e.g., by inhalation), subcutaneous (e.g., by absorption into the skin from an implant containing the compound or composition), or by other route.

As used herein, the term "Adrenocorticotrophic Hormone" (ACTH) refers to the peptide hormone produced and secreted by the anterior pituitary gland that stimulates the adrenal cortex to secrete glucocorticoid hormones, which help cells synthesize glucose, catabolize proteins, mobilize free fatty acids and inhibit inflammation in allergic responses. One such glucocorticoid hormone is cortisol, which regulates metabolism of carbohydrate, fat, and protein metabolism. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids.

The term "measuring the level," in the context of ACTH, cortisol, or other analyte, refers determining, detecting, or quantitating the amount, level, or concentration of, for example, cortisol, ACTH or other steroid in a sample obtained from a subject. The sample may be, e.g., a blood sample, a saliva sample, a urine sample, or other sample obtained from the patient. A level may be measured from a fraction of a sample. For example, a level (e.g., ACTH or cortisol) may be measured in the plasma fraction of a blood sample; may be measured in a serum fraction of a blood sample; or, in embodiments, may be measured in whole blood; may be measured in saliva; may be measured in urine; or measured in other bodily fluids.

The term "cortisol" refers to the naturally occurring glucocorticoid hormone (also known as hydrocortisone) that is produced by the zona fasciculata of the adrenal gland. Cortisol has the structure:

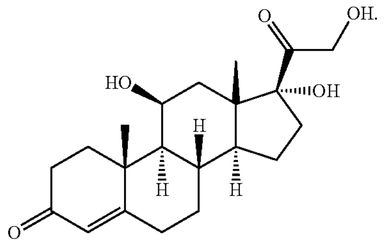

The term "total cortisol" refers to cortisol that is bound to cortisol-binding globulin (CBG or transcortin) and free cortisol (cortisol that is not bound to CBG). The term "free cortisol" refers to cortisol that is not bound to cortisol-binding globulin (CBG or transcortin). As used herein, the term "cortisol" refers to total cortisol, free cortisol, and/or cortisol bound of CBG.

Cortisol levels may be measured in blood (e.g., serum or plasma), urine, saliva, and other bodily fluids. Urinary free cortisol (UFC, a measure of cortisol in urine excreted over 24 hours) is a common cortisol level measurement method, which masks the daily cortisol variations by requiring a full day's sample. Plasma cortisol (a measure of the cortisol levels at the time the blood sample is taken) is often used for dexamethasone suppression testing (which tests patient response to rapid increases in glucocorticoid levels). In addition, cortisol level can also be measured in a serum sample according to methods known in the art. Salivary cortisol may also be measured. The numerical value of the cortisol level differs between measurement methods; that is, blood cortisol levels (e.g., serum or plasma levels) sample cortisol at the time the blood sample is taken, and are numerically different than salivary cortisol levels (sample cortisol at the time the saliva sample is taken) and numerically different than urinary free cortisol levels (which represent cortisol levels over a 24-hour period).

The level of cortisol can be measured in a sample (of, e.g., serum, plasma, saliva, urine, or any other biological fluid) using various methods, including but not limited to, immunoassays, e.g., competitive immunoassay, radioimmunoassay (MA), immunofluorometric enzyme assay, and ELISA; competitive protein-binding assays; liquid chromatography (e.g., HPLC); and mass spectrometry, e.g., high-performance liquid chromatography/triple quadrupole-mass spectrometry (LC-MS/MS). In preferred embodiments, cortisol levels are measured using LC-MS/MS, such as performed by Quest Diagnostics (Secaucus, N.J. 07094).

The term "normal level" refers to the average level of an analyte as determined by measurements of samples obtained from multiple normal subjects. For comparison, the same types of measurements (e.g., plasma or serum; salivary; or urinary) must be the compared.

The term "normal cortisol level" refers to the average level of cortisol as determined by measurements of samples (e.g., serum samples) obtained from multiple normal subjects. For example, as reported by Putignano et al. (European Journal of Endocrinology 145: 165-171 (2001)), normal plasma cortisol in healthy women was about 420 nanomoles per liter (nmol/1) at 8 AM (morning); about 250 nmol/1 at 5 PM (evening); and about 90 nmol/1 at 12 PM (late night). Salivary cortisol measurements from these women were about 14 nmol/1 at 8 AM (morning); about 7 nmol/1 at 5 PM (evening); and about 5 nmol/1 at 12 PM (late night). Urinary free cortisol levels measured in these healthy women were about 130 nmol per 24 hours (nmol/24 h). Cortisol levels are suppressed by the dexamethasone suppression test (DST), as indicated by the plasma cortisol level of about 24 nmol/1 following DST and the salivary cortisol level of about 4 nmol/1 following DST.

Applicant has discovered that measurement of cortisol levels of a patient having an ACC tumor allows identification of those patients who would benefit from combined SGRM and antibody checkpoint inhibitor treatment, by determining whether or not the patient has cortisol excess.

As used herein, the term "cortisol excess" refers to cortisol levels, however measured, that are greater than about 1.5 times, or greater than about 2 times, the cortisol levels measured in healthy subjects (where the healthy subject cortisol levels are measured by the same methods as the patient's cortisol is measured). For example, using the morning plasma cortisol levels of Putignano et al., cortisol excess would be determined if a patient had morning plasma cortisol levels of about 630 nmol/1 or greater, or of about 840 nmol/1 or greater. Using the morning salivary cortisol levels of Putignano et al., cortisol excess would be determined if a patient had morning salivary cortisol levels of about 21 nmol/1 or greater, or of about 28 nmol/1 or greater. Using the 24-hour urinary free cortisol levels of Putignano et al., cortisol excess would be determined if a patient had 24-hour urinary cortisol levels of about 195 nmol/24 h or greater, or of about 260 nmol/24 h or greater.

In embodiments, combined criteria may be used to identify patients with cortisol excess. For example, two or more, or all, or the following criteria may be used to determine whether or not a patient suffers from cortisol excess:

1. Urinary Free Cortisol (UFC) greater than the upper limit of normal (ULN)
2. Late night salivary cortisol (LNSC) greater than ULN for 2 nights
3. Dexamethasone Suppression Test (DST) with cortisol level greater than 1.8 μg/dL
4. Adrenocorticotrophic Hormone (ACTH) less than 10 picogram per milliliter (pg/mL)

"Standard control" as used herein refers to a sample comprising a predetermined amount of an analyte (such as ACTH or cortisol) suitable for the use of an application of the present invention, in order to serve as a comparison basis for providing an indication of the relative amount of the analyte (e.g., ACTH or cortisol) that is present in a test sample. A sample serving as a standard control provides an average amount of an analyte such as ACTH or cortisol that is representative for a defined sample type (e.g., plasma, serum, saliva, or urine) taken at a defined time of the day (e.g., 8 AM) from an average individual who is not suffering from or at increased risk of later developing hypokalemia or any associated disorder or complication and has been given the same GRM treatment. As used herein, a "blood sample" may be a whole blood sample, serum sample, plasma sample, or blood cell sample as appropriate for measuring an analyte level by art-known methods according to conventional use. Similarly, "blood level" of a particular analyte maybe the level of the analyte in the whole blood, serum, plasma, or blood cells. For example, the blood level of potassium, ACTH, or cortisol maybe the level of each analyte in a serum or plasma sample taken from a subject being tested.

The term "average," as used in the context of describing an individual (especially a human subject) who does not have and is not at increased risk of developing hypokalemia or any related condition or disorder prior to receiving GRM treatment, refers to certain characteristics, such as the level or amount of an analyte (such as ACTH or cortisol) present in a sample taken from the individual without receiving GRM treatment, that are representative of the average amount or level of the analyte found in a randomly selected group of individual subjects who have not been diagnosed with and are not susceptible to hypokalemia or any related diseases or conditions and therefore can serve as an "average normal value" or "standard control value" for the particular analyte prior to GRM treatment. This selected group should comprise a sufficient number of individuals (e.g., at least 200 or 500 or more) such that the average value (i.e., level or amount) of the analyte of interest (e.g., ACTH or cortisol) assessed among these individuals reflects, with reasonable accuracy, the corresponding level or amount of the analyte found in the general population of non-hypokalemic individuals with no known risk for the disorder or related conditions upon receiving GRM treatment. In some cases, the selected group of individuals generally have the same gender, are similar in age (e.g., within a 5- or 10-year age difference from one another), have similar ethnic and medical backgrounds. Depending on the analyte, the average value or standard control value may need to be ascertained from samples taken from these individuals at about the same time during the day (e.g., 6 AM, 8 AM, 12 PM, 4 PM, or 6 PM). The average or standard control value of any particular analyte may also vary depending on the specific assay or assay format (including the specific reagents) utilized for quantitatively measuring the analyte, and therefore can be made available either by way of experimentation or by way of assay manufacturer's information.

The term "glucocorticosteroid" ("GC") or "glucocorticoid" refers to a steroid hormone that binds to a glucocorticoid receptor. Glucocorticosteroids are typically characterized by having 21 carbon atoms, an α,β-unsaturated ketone in ring A, and an α-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567. Cortisol is a glucocorticosteroid.

A mineralocorticoid receptor (MR), also known as a type I glucocorticoid receptor (GR I), is activated by aldosterone in humans.

As used herein, the term "glucocorticoid receptor" ("GR") refers to the type II GR, a family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

The term "glucocorticoid receptor modulator" (GRM) refers to any compound which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

As used herein, the term "selective glucocorticoid receptor modulator" (SGRM) refers to any composition or compound which modulates any biological response associated with the binding of a GR to an agonist. By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor modulator bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the selective glucocorticoid receptor modulator binds GR with an affinity that is 100× greater ($1/100^{th}$ the $K_d$ value) than its affinity to the MR, AR, or PR, both the MR and PR, both the MR and AR, both the AR and PR, or to the MR, AR, and PR. In another embodiment, the selective glucocorticoid receptor modulator binds GR with an affinity that is 1000× greater ($1/1000^{th}$ the $K_d$ value) than its affinity to the MR, AR, or PR, both the MR and PR, both the MR and AR, both the AR and PR, or to the MR, AR, and PR. Relacorilant is a SGRM.

"Glucocorticoid receptor antagonist" (GRA) refers to any compound which inhibits any biological response associated with the binding of GR to an agonist. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. An antagonist is a compound with an $IC_{50}$ (half maximal inhibition concentration) of less than 10 micromolar. See Example 1 of U.S. Pat. No. 8,859,774, the entire contents of which is hereby incorporated by reference in its entirety.

As used herein, the term "selective glucocorticoid receptor antagonist" (SGRA) refers to any composition or compound which inhibits any biological response associated with the binding of a GR to an agonist (where inhibition is determined with respect to the response in the absence of the compound). By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor antagonist bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the selective glucocorticoid receptor antagonist binds GR with an affinity that is 100× greater ($1/100^{th}$ the $K_d$ value) than its affinity to the MR, AR, or PR, both the MR and PR, both the MR and AR, both the AR and PR, or to the MR, AR, and PR. In another embodiment, the selective glucocorticoid receptor antagonist binds GR with an affinity that is 1000× greater ($1/1000^{th}$ the $K_d$ value) than its affinity to the MR, AR, or PR, both the MR and PR, both the MR and AR, both the AR and PR, or to the MR, AR, and PR. Relacorilant (CORT125134) is a SGRA.

As used herein, the phrase "not otherwise indicated for treatment with a glucocorticoid receptor modulator" refers to refers to a patient that is not suffering from any condition recognized by the medical community to be effectively treatable with glucocorticoid receptor antagonists, with the exception of hepatic steatosis. Conditions known in the art and accepted by the medical community to be effectively treatable with glucocorticoid receptor antagonists include: psychosis associated with interferon-α therapy, psychotic major depression, dementia, stress disorders, autoimmune disease, neural injuries, and Cushing's syndrome, The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

As used herein, the term "checkpoint inhibitor sensitive cancer" refers to a cancer that is responsive to checkpoint inhibitors. Administration of one or more checkpoint inhibitors to patients having such a tumor would cause a reduction in the ACC tumor load, restore T-cell and natural killer (NK) cell signaling pathways, increase T-cell and NK cell infiltration into the ACC tumor, and reduce neutrophil infiltration into the ACC tumor in the patient, or other desired beneficial clinical outcome related to cancer improvement.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. The effective amount can be an amount effective to invoke an antitumor response. The effective amount can be an amount effective to evoke a therapeutically beneficial response (e.g., an antitumor, a humoral, and/or cellular immune response) in the recipient subject, e.g., leading to growth inhibition or death of target cells. For the purpose of this disclosure, the effective amount of the SGRM or the effective amount of an antibody checkpoint inhibitor (and optionally a chemotherapeutic agent) is an amount that would reduce ACC tumor load, restore T-cell and natural killer (NK) cell signaling pathways, increase T-cell and NK cell infiltration into the ACC tumor, reduce neutrophil infiltration into the ACC tumor in the patient, or bring about other desired beneficial clinical outcomes related to cancer improvement.

As used herein, the phrase "an amount effective to potentiate" refers to the amount of a pharmacological agent that is effective to enhance the activity of another therapeutic agent in treating, eliminating, or mitigating at least one symptom of the disease being treated. For example, an effective amount of a SGRM administered in combination with an antibody checkpoint inhibitor is that amount of the SGRM that improves the therapeutic response to that antibody checkpoint inhibitor. The agent used to potentiate the activity of another can be effective or non-effective in treating, eliminating, or mitigating the symptom of the disease itself. In some cases, the potentiating agent is not effective, and the effect of potentiation can be shown by the increased degree in relieving the symptom resulting from treatment by the combination of the two agents as compared to the treatment with the therapeutic agent alone. In some cases, the potentiating agent itself is effective in treating the symptoms, and the potentiating effect can be shown by a synergistic effect between the potentiating agent and the therapeutic agent. For the purpose of this disclosure, the SGRM acts as a potentiating agent to potentiate the activity of checkpoint inhibitors in treating cancer, regardless whether the SGRM would be effective in treating the cancer if administered alone. In some embodiments, a potentiating effect of 10% to 1000% can be achieved. In some embodiments, the SGRM is administered at an amount that renders the tumor sensitive to the checkpoint inhibitor, i.e., a showing of a reduction of ACC tumor load, restore T-cell and natural killer (NK) cell signaling pathways, increase T-cell and NK cell infiltration into the ACC tumor, reduce neutrophil infiltration into the ACC tumor in the patient, or other related clinical benefit that would not otherwise appear when the tumor is treated with the antibody checkpoint inhibitor in the absence of the SGRM.

As used herein, the term "combination therapy" refers to the administration of at least two pharmaceutical agents to a subject to treat a disease. The two agents may be administered simultaneously, or sequentially in any order during the entire or portions of the treatment period. The two agents may be administered following the same or different dosing regimens. In some cases, one agent is administered following a scheduled regimen while the other agent is administered intermittently. In some cases, both agents are administered intermittently. In some embodiments, the one pharmaceutical agent, e.g., a SGRM, is administered every day, and the other pharmaceutical agent, e.g., an antibody checkpoint inhibitor, is administered every two, three, or four days, or weekly or biweekly.

As used herein, the term "co-administer" refers to administer two compositions simultaneously or within a short time of each other, e.g., within about within 0.5, 1, 2, 4, 6, 8, 10, 12, 16, 20, or 24 hours of each other.

As used herein, the term "checkpoint protein" refers to a protein that is present on the surface of certain types of cells, e.g. T cells and certain tumor cells, and can induce checkpoint signaling pathways and result in suppression of immune responses. Commonly known checkpoint proteins include CTLA4, PD-1, PD-L1, LAG3, B7-H3, B7-H4, CD160, CD244, VISTA, TIGIT, and BTLA. (Pardoll, 2012, Nature Reviews Cancer 12:252-264; Baksh, 2015, Semin Oncol. 2015 June; 42(3):363-77). Among these, CTLA4, PD-1 and PD-L1 are most well studied and therapies targeting these proteins are more clinically advanced than therapies targeting other checkpoint proteins.

As used herein, the term "PD-1" refers to Programmed Cell Death Protein 1 (also known as CD279), a cell surface membrane protein of the immunoglobulin superfamily. PD-1 is expressed by B cells, T cells and NK cells. The major role of PD-1 is to limit the activity of T cells in peripheral tissues during inflammation in response to infection, as well as to limit autoimmunity. PD-1 expression is induced on activated T cells and binding of PD-1 to one of its endogenous ligands acts to inhibit T cell activation by inhibiting stimulatory kinases. PD-1 also acts to inhibit the TCR "stop signal". PD-1 is highly expressed on Treg cells (regulatory T cells) and may increase their proliferation in the presence of ligand (Pardoll, 2012, Nature Reviews Cancer 12:252-264).

As used herein, the term "PD-L1" refers to Programmed Cell Death 1 ligand 1 (also known as CD274 and B7-H1), a ligand for PD-1. PD-L1 is found on activated T cells, B cells, myeloid cells, macrophages, and tumor cells. Although there are two endogenous ligands for PD-1, PD-L1 and PD-L2, anti-tumor therapies have focused on anti-PD-L1. The complex of PD-1 and PD-L1 inhibits proliferation of CD8+ T cells and reduces the immune response (Topalian et al., 2012, *N. Engl J. Med.* 366:2443-54; Brahmer et al., 2012, *N. Engl J. Med.* 366:2455-65).

As used herein, the term "CTLA4" refers to Cytotoxic T-lymphocyte antigen 4 (also known as CD152), a member of the immunoglobulin superfamily that is expressed exclusively on T cells. CTLA4 acts to inhibit T cell activation and is reported to inhibit helper T cell activity and enhance regulatory T cell immunosuppressive activity. Although the precise mechanism of action of CTL4-A remains under investigation, it has been suggested that it inhibits T cell activation by outcompeting CD28 in binding to CD80 and CD86 on antigen presenting cells, as well as actively delivering inhibitor signals to the T cell (Pardoll, 2012, Nature Reviews Cancer 12:252-264).

As used herein, the term "checkpoint inhibitor" refers to any molecules, including antibodies and small molecules, that block the immunosuppression pathway induced by one or more checkpoint proteins. Therapy that utilizes a checkpoint inhibitor to treat a disorder, such as cancer, may be termed immune system checkpoint inhibitor therapy; the acronym "ICI" refers to immune system checkpoint inhibitor. In embodiments, ICI therapy utilizes antibody checkpoint inhibitors, comprising administering an antibody checkpoint inhibitor to a patient in need of such therapy, which may be combination therapy including a GRM, SGRM, GRA, or SGRA in combination with an antibody checkpoint inhibitor. In embodiments, ICI therapy utilizes small molecule checkpoint inhibitors, comprising administering a small molecule checkpoint inhibitor to a patient in need of such therapy, which may be combination therapy including a GRM, SGRM, GRA, or SGRA in combination with a small molecule checkpoint inhibitor.

As used herein, the term "antibody checkpoint inhibitor" refers to antibodies that block the immunosuppression pathway induced by one or more checkpoint proteins. Therapy that utilizes a checkpoint inhibitor to treat a disorder, such as cancer, may be termed, for example, antibody checkpoint inhibitor therapy. In embodiments, antibody checkpoint inhibitor therapy comprises administering an antibody checkpoint inhibitor to a patient in need of such therapy, which may be combination therapy including a GRM, SGRM, GRA, or SGRA in combination with an antibody checkpoint inhibitor.

As used herein, the term "antibody effective against a checkpoint protein" refers to an antibody that can bind to the checkpoint protein and antagonize the checkpoint protein's function in suppressing immune response. For example, an antibody against PD-1 refers to an antibody that can bind to PD-1 and block the PD-1's inhibitory function on the immune response, through e.g., blocking the interactions between PD-1 and PD-L1. In some cases, an antibody can be against two checkpoint proteins, i.e., having the ability of binding to two checkpoint proteins and inhibiting their function. An "antibody effective against a checkpoint protein" is an "antibody checkpoint inhibitor".

As used herein, the term "antibody" as used herein also includes a full-length antibody as well as an "antigen-binding portion" of an antibody. The term "antigen-binding portion", as used herein, refers to one or more fragments of an antibody that retain the ability to specifically bind to an antigen (e.g., PD-1). Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and VI can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Antibodies may be polyclonal or monoclonal; xenogeneic, allogeneic, or syngeneic; or modified forms thereof, e.g. humanized, chimeric, etc. Antibodies of the invention bind specifically or substantially specifically to one or more checkpoint proteins. The term "monoclonal antibodies" refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition typically displays a single binding affinity for a particular antigen with which it immunoreacts.

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to, cyclopropyl, cyclobutyl, cyclopentyl, cyclohexyl, cycloheptyl, and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and $—S(O)_2—$. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —$S(O)_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6-pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline; quinazoline includes 2- and 4-quinoazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods of the present invention. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

Non-steroidal SGRM compounds include SGRMs having a fused azadecalin backbone, a heteroaryl ketone fused azadecalin backbone, and an octahydro fused azadecalin backbone. Exemplary glucocorticoid receptor modulators having a fused azadecalin backbone include those described in U.S. Pat. Nos. 7,928,237 and 8,461,172. Exemplary glucocorticoid receptor modulators having a heteroaryl ketone fused azadecalin backbone include those described in U.S. Pat. No. 8,859,774. Exemplary glucocorticoid receptor modulators having an octahydro fused azadecalin backbone include those described in U.S. Pat. No. 10,047,082.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. As used herein, these terms are intended to include any and all solvents, dispersion media, coatings, antibacterial and antifungal agents, antioxidant agents, isotonic and absorption delaying agents, and the like, compatible with pharmaceutical administration. Non-limiting examples of pharmaceutically-acceptable excipients include water, NaCl, normal saline solutions, lactated Ringer's, normal sucrose, normal glucose, binders, fillers, disintegrants, encapsulating agents, plasticizers, lubricants, coatings, sweeteners, flavors and colors, and the like. One of ordinary skill in the art will recognize that other pharmaceutical excipients are useful in the present invention. The use of such media and agents for pharmaceutically active substances is well known in the art. Except insofar as any conventional media or agent is incompatible with the active compound, use thereof in the compositions is contemplated. Supplementary active compounds can also be incorporated into the compositions. One of ordinary skill in the art will recognize that other pharmaceutical excipients are useful in the present invention.

Methods of treating ACC tumors in patients with cortisol excess by treatment with a combination of SGRM treatment and treatment with an antibody checkpoint inhibitor are disclosed herein. In embodiments, the cancer is a checkpoint inhibitor sensitive cancer. In embodiments, the checkpoint inhibitor sensitive cancer is also a $GR^+$ cancer.

Diagnosing Cancer

The present methods are directed to treating patients suffering from adrenocortical carcinoma (ACC). Cancers are characterized by uncontrolled growth and/or spread of abnormal cells. A biopsy is typically taken and the cell or tissue from the biopsy is examined under a microscope in order to confirm a suspected condition. In some cases, additional tests need to be performed on the cells' proteins, DNA, and RNA to verify the diagnosis.

Identifying Checkpoint Inhibitor Sensitive Cancer

In some embodiments of the invention, methods are used to treat patients having at least one checkpoint inhibitor sensitive cancer. Checkpoint inhibitor sensitive cancers are those that are responsive to checkpoint inhibitors, i.e., administration of one or more checkpoint inhibitors can reduce ACC tumor load, or achieve beneficial or desired clinical results related to cancer improvement. For example, the administration of the checkpoint inhibitor may bring about one or more of the following: reducing the number of cancer cells; reducing the tumor size; inhibiting (i.e., slowing to some extent and/or stop) cancer cell infiltration into peripheral organs; inhibiting (i.e., slowing to some extent and/or stop) tumor metastasis; inhibiting, to some extent, tumor growth; and/or relieving to some extent one or more of the symptoms associated with the disorder; shrinking the size of the tumor; decreasing symptoms resulting from the disease; increasing the quality of life of those suffering from the disease; decreasing the dose of other medications required to treat the disease; delaying the progression of the disease; and/or prolonging survival of patients.

Checkpoint inhibitor sensitive tumors often have high expression of ligands, e.g., PD-L1 or B7, that bind to checkpoint proteins, PD-1 or CTLA-4, respectively. These interactions suppress immune responses against the tumor cells. In addition to ACC, non-limiting examples of checkpoint inhibitor sensitive tumors include lung cancer, liver cancer, ovarian cancer, cervical cancer, skin cancer, bladder cancer, colon cancer, breast cancer, glioma, renal carcinoma, stomach cancer, esophageal cancer, oral squamous cell cancer, head/neck cancer, melanoma, sarcoma, renal cell tumor, hepatocellular tumor, glioblastoma, neuroendocrine tumor, bladder cancer, pancreatic cancer, gall bladder cancer, gastric cancer, prostate cancer, endometrial cancer, thyroid cancer and mesothelioma.

Checkpoint Inhibitors

The method disclosed herein uses at least one SGRM in combination with at least one checkpoint inhibitor to treat cancers. In some embodiments, the checkpoint inhibitor is an antibody ("CIA") against at least one checkpoint protein. In some embodiments, the checkpoint inhibitor is a small molecule, non-protein compound ("CIC") that blocks the immunosuppression pathway induced by one or more checkpoint proteins.

Checkpoint Inhibitor Antibodies ("CIA", Also "Antibody Checkpoint Inhibitors")

In one embodiment, the method for treating cancer comprises administering a SGRM in combination with an antibody checkpoint inhibitor antibody. Such an antibody can block the immunosuppression activity of the checkpoint protein. A number of such antibodies have already been shown to be effective in treating cancers, e.g., antibodies against PD-1, CTLA4, and PD-L1.

Anti-PD-1 antibodies have been used for the treatment of melanoma, non-small-cell lung cancer, bladder cancer, prostate cancer, colorectal cancer, head and neck cancer, triple-negative breast cancer, leukemia, lymphoma and renal cell cancer. Exemplary anti-PD-1 antibodies include pembrolizumab (formerly lambrolizumab; MK-3475, MERCK), nivolumab (BMS-936558, BRISTOL-MYERS SQUIBB), AMP-224 (MERCK), and pidilizumab (CT-011, CURETECH LTD.).

Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies. Exemplary anti-PD-L1 antibodies include MDX-1105 (MEDAREX), MEDI4736 (MEDIMMUNE), atezolizumab (MPDL3280A; GENENTECH), durvalumab (AstraZeneca), and BMS-936559 (BRISTOL-MYERS SQUIBB).

Anti-CTLA4 antibodies have been used in clinical trials for the treatment of melanoma, prostate cancer, small cell lung cancer, non-small cell lung cancer. A significant feature of anti-CTL4A is the kinetics of anti-tumor effect, with a lag period of up to 6 months after initial treatment required for physiologic response. In some cases, tumors may actually increase in size after treatment initiation, before a reduction is seen (Pardoll, 2012, Nature Reviews Cancer 12:252-264). Exemplary anti-CTLA4 CIAs include ipilimumab (Bristol-Myers Squibb) and tremelimumab (PFIZER).

CIAs against other checkpoint proteins, such as, e.g., LAG-3 (lymphocyte activation gene-3), B7-H3 (B7 homolog 3 protein), B7-H4 (B7 homolog 4 protein), TIM-3 (T-cell immunoglobulin and mucin domain-3), CD160, CD244, VISTA (V-domain Ig suppressor of T cell activation), TIGIT (T cell immunoglobulin and ITIM domain), and BTLA (B and T cell lymphocyte attenuator) may also be used in combination with the SGRMs disclosed herein to treat cancers. For example, antibodies that inhibit LAG-3 include IMP321/Eftilagimod alpha (Immutep), Relatlimab (BMS-986016, Bristol Myers Squibb (BMS)), LAG525 (Novartis), and MK-4280 (Merck). Antibodies that inhibit B7-H3 include Enoblituzumab/MGA271 (MacroGenics), MGD009e (MacroGenics), $^{131}$I-8H9/omburtamab (Y-mAbs), and $^{124}$I-8H9/omburtamab (Y-mAbs). Antibodies that inhibit TIM-3 include LY3321367 (also known as LY332; Eli Lilly and Company), TSR-022 (Tesaro), MBG453 (Novartis), Sym023 (Symphogen), INCAGN2390 (Incyte), BMS-986258 (BMS), RO7121661 (Roche), and SHR-1702 (Jiangsu HengRui); LY3321367, for example, has shown promise in early clinical trials, including when used in combination with PD-L1 checkpoint inhibitors. Antibodies that inhibit VISTA include JNJ-61610588 (Johnson & Johnson) and CA-170[d] (Curis). Antibodies that inhibit TIGIT include MK-7684 (Merck), Tiragolumab/MTIG7192A/RG-6058 (Genentech), Etigilimab/OMP-313 M32 (OncoMed), BMS-986207 (BMS), AB-154 (Arcus Biosciences), and ASP-8374 (Potenza).

The CIAs used in this disclosure can be a combination of different CIAs, especially if the target checkpoint proteins, e.g., PD-1 and CTLA4, suppress immune response via different signaling pathways. Thus a combination of CIAs against either of the checkpoint proteins or a single CIA that is against both checkpoint proteins may provide an enhanced immune response.

Generating CIAs

CIAs can be developed using methods well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Monoclonal antibodies can be obtained by injecting mice with a composition comprising an antigen, e.g. a checkpoint protein or an epitope of thereof, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Monoclonal antibodies produced can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to a checkpoint protein, the antibodies can be sequenced and subsequently prepared by recombinant techniques. Humanization and chimerization of murine antibodies and antibody fragments are well known to those skilled in the art. See, for example, Leung et al. Hybridoma 13:469 (1994); US20140099254 A1.

Human antibodies can be produced using transgenic mice that have been genetically engineered to produce specific human antibodies in response to antigenic challenge using a checkpoint protein. See Green et al., Nature Genet. 7: 13 (1994), Lonberg et al., Nature 368:856 (1994). Human antibodies against a checkpoint protein also can be constructed by genetic or chromosomal trandfection methods, phage display technology, or by in vitro activated B cells. See e.g., McCafferty et al., 1990, Nature 348: 552-553; U.S. Pat. Nos. 5,567,610 and 5,229,275.

Modifying CIAs

CIAs may also be produced by introducing conservative modifications relative to the existing CIAs. For example, a modified CIA may comprise heavy and light chain variable regions, and/or a Fc region that are homologous to the counterparts of an antibody produced above. The modified CIA that can be used for the method disclosed herein must retain the desired functional properties of being able to block the checkpoint signaling pathway.

CIAs may also be produced by altering protein modification sites. For example, sites of glycosylation of the antibody can be altered to produce an antibody lacking glycosylation and the so modified CIAs typically have increased affinity of the antibody for antigen. Antibodies can also be pegylated by reacting with polyethylene glycol (PEG) under conditions in which one or more PEG groups become attached to the antibody. Pegylation can increase the biological half-life of the antibody. Antibodies having such modifications can also be used in combination with the selective GR modulator disclosed herein so long as it retains the desired functional properties of blocking the checkpoint pathways.

iii. Evaluating the Functional Properties of the Candidate Checkpoint Inhibitors A number of well-known assays can be used to assess whether a candidate, i.e., an antibody generated by immunizing an animal with an antigen comprising a checkpoint protein, an epitope of the checkpoint protein, or a test compound from combinatorial libraries, as disclosed above, is an antibody checkpoint inhibitor. Non-limiting exemplar assays include binding assays—such as Enzyme-Linked Immunosorbent Assays (ELISAs), radioimmunoassays (RIA)—, Fluorescence-Activated Cell Sorting (FACS) analysis, cell-based assays, and in vivo assays.

Binding Assays

In one embodiment, the assay is a direct binding assay. The checkpoint protein can be coupled with a radioisotope or enzymatic label such that binding of the checkpoint protein and the candidate can be determined by detecting the labeled checkpoint protein in a complex. For example, a checkpoint protein can be labeled with $^{125}I$, $^{35}S$, $^{14}C$, or $^{3}H$, either directly or indirectly, and the radioisotope detected by direct counting of radio-emission or by scintillation counting. Determining the ability of candidates to bind their cognate checkpoint protein can be accomplished, e.g., by measuring direct binding. Alternatively, checkpoint protein molecules can be enzymatically labeled with, for example, horseradish peroxidase, alkaline phosphatase, or luciferase, and binding of the candidates to the target checkpoint protein is determined by conversion of an appropriate substrate to product.

Enzyme-linked immunosorbent assay (ELISA) are commonly used to evaluate a CIA candidate's binding specificity to its target checkpoint protein. In a typical assay, microtiter plates are coated with the checkpoint protein by coating overnight at 37° C. with 5 μg/ml checkpoint protein. Serum samples comprising candidate CIAs are diluted in PBS, 5% serum, 0.5% Tween-20 and are incubated in wells for 1 hour at room temperature, followed by the addition of anti-human IgG Fc and IgG F(ab')-horseradish peroxidase in the same diluent. After 1 hour at room temperature enzyme activity is assessed by addition of ABTS substrate (Sigma, St. Louis Mo.) and read after 30 minutes at 415-490 nm.

The binding kinetics (e.g., binding affinity) of the candidates also can be assessed by standard assays known in the art, such as by Biacore analysis (Biacore AB, Uppsala, Sweden). In one exemplary assay, a purified recombinant human checkpoint protein is covalently linked to a CMS chip (carboxy methyl dextran coated chip) via primary amines, using standard amine coupling chemistry and kit provided by Biacore. Binding is measured by flowing the candidates in HBS EP buffer (provided by Biacore AB) at a concentration of 267 nM at a flow rate of 50 μl/min. The checkpoint protein-candidate association kinetics are followed for 3 minutes and the dissociation kinetics are followed for 7 minutes. The association and dissociation curves are fitted to a 1:1 Langmuir binding model using BIA evaluation software (Biacore AB). To minimize the effects of avidity in the estimation of the binding constants, only the initial segment of data corresponding to association and dissociation phases are used for fitting. The $K_D$, $K_{on}$ and $K_{off}$ values of the interaction can be measured. Preferred checkpoint inhibitors can bind to their target checkpoint protein with a Kd of $1\times10^{-7}$M or less For checkpoint proteins that block immune responses through binding to a ligand, additional binding assays may be employed to test for the ability of the candidate to block binding of the ligands to the checkpoint protein. In one exemplary assay, flow cytometry is used to test the blocking of the binding of the ligand (e.g., PD-L1) to the checkpoint protein (e.g., PD-1) expressed on transfected CHO cells. Various concentrations of the candidate are added to the suspension of cells expressing the checkpoint protein and incubated at 4° C. for 30 minutes. Unbound inhibitor is washed off and FITC-labeled ligand protein is added into the tubes and incubated at 4° C. for 30 minutes. FACS analysis is performed using a FACScan flow cytometer (Becton Dickinson, San Jose, Calif.). The mean fluorescent intensity (MFI) of staining of the cells indicates the amount of ligand that is bound to the checkpoint proteins. A reduced MFI in the sample to which the candidate is added indicates that the candidate is effective in blocking the binding of the ligand to the target checkpoint protein.

Homogenous Time-Resolved Fluorescence (HTRF) binding assay, such as described in PCT publication WO2015034820, can also be used to assay the candidate's ability to block the checkpoint protein-ligand interaction. In one embodiment, the CICs used in the method can inhibit the PD-1/PD-L1 interaction with $IC_{50}$ values of 10 pM or less, for example, from 0.01 to 10 pM, preferrably, 1 pM or less, e.g., from 0.01 to 1 pM, as measured by the PD-1/PD-L1 Homogenous Time-Resolved Fluorescence (HTRF) binding assay.

Cell Based Assays

In another embodiment, the assay to evaluate whether a candidate is an antibody checkpoint inhibitor is a cell based assay. The Mixed Lymphocyte Reaction (MLR) assay, as described in U.S. Pat. No. 8,008,449, is routinely used to measure T cell proliferation, production of IL-2 and/or IFN-γ. In one exemplary assay, human T cells are purified from PBMCs using a human $CD4^+$ T cell enrichment column (R&D systems). A candidate is added to a number of T cell cultures at different concentrations. The cells are cultured for 5 days at 37° C. and 100 μl of medium is taken from each culture for cytokine measurement. The levels of IFN-gamma and other cytokines are measured using OptEIA ELISA kits (BD Biosciences). The cells are labeled with $^{3}H$-thymidine, cultured for another 18 hours, and analyzed for cell proliferation. Results showing that, as compared to control, the culture containing the candidate shows increased T cell proliferation, increased production of IL-2, and/or IFN-gamma indicate the candidate is effective in blocking checkpoint protein's inhibition of T cell immune response.

In Vivo Assays

In another embodiment, the assay used to evaluate whether a candidate is an antibody checkpoint inhibitor is a in vivo assay. In one exemplary assay, female AJ mice between 6-8 weeks of age (Harlan Laboratories) are randomized by weight into 6 groups. The mice are implanted subcutaneously in the right flank with $2\times10^{6}$ SA1/N fibrosarcoma cells dissolved in 200 μl of DMEM media on day 0. The mice are treated with PBS vehicle, or the candidate at a predetermined dosage. The animals are dosed by intraperitoneal injection with approximately 200 μl of PBS containing the candidate or vehicle on days 1, 4, 8 and 11. The mice are monitored twice weekly for tumor growth for approximately 6 weeks. Using an electronic caliper, the tumors are measured three dimensionally (height×width×length) and tumor volume is calculated. Mice are euthanized when the tumors reach tumor end point (1500 $mm^3$) or the mice show greater than 15% weight loss. A result showing that a slower tumor growth in the candidate treated group as compared to controls, or a longer mean time to reach the tumor end point volume (1500 $mm^3$) is an indication that the candidate has activity in inhibiting cancer growth.

Glucocorticoid Receptor Modulators (GRM)

Generally, treatment of adrenocortical carcinomas (ACC) in patients with glucocorticoid excess can be provided by administering an effective amount of a selective glucocorticoid receptor modulator (SGRM) having a fused azadecalin structure, a heteroaryl-ketone fused azadecalin structure, or an octandro fused azadecalin structure, and an antibody checkpoint inhibitor. In embodiments, the antibody checkpoint inhibitor is effective against cells and tumors expressing one or more of the antigens PD-1, CTLA-4, PD-L1, or PD-L2. In embodiments, a cancer chemotherapy agent may also be administered. The cancer chemotherapy agent may be, for example, selected from taxanes, alkylating agents, topoisomerase inhibitors, endoplasmic reticulum stress inducing agents, antimetabolites, mitotic inhibitors and combinations thereof.

Selective glucocorticoid receptor modulators (SGRM) compounds include compounds comprising a heteroaryl-ketone fused azadecalin structure (which may also be termed a heteroaryl-ketone fused azadecalin backbone). Exemplary SGRM compounds comprising a heteroaryl ketone fused azadecalin structure include those described in U.S. Pat. No. 8,859,774; in U.S. Pat. No. 9,273,047; in U.S. Pat. No. 9,707,223; and in U.S. Pat. No. 9,956,216. All patents, patent publications, and patent applications disclosed herein are hereby incorporated by reference in their entireties.

In some cases, the GRM backbone is a fused azadecalin. In some cases, the GRM having a fused azadecalin backbone is a SGRM, and may be a GRA or a SGRA. In some cases, the fused azadecalin is a compound having the following formula:

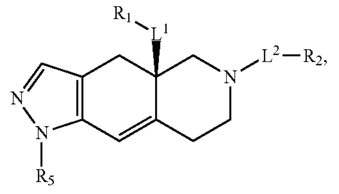

wherein $L^1$ and $L^2$ are members independently selected from a bond and unsubstituted alkylene; $R^1$ is a member selected from unsubstituted alkyl, unsubstituted heteroalkyl, unsubstituted heterocycloalkyl, —$OR^{1A}$, $NR^{1C}R^{1D}$, —C(O)$NR^{1C}R^{1D}$, and —C(O)$OR^{1A}$, wherein $R^{1A}$ is a member selected from hydrogen, unsubstituted alkyl, and unsubstituted heteroalkyl; $R^{1C}$ and $R^{1D}$ are members independently selected from unsubstituted alkyl and unsubstituted heteroalkyl, and are optionally joined to form an unsubstituted ring with the nitrogen to which they are attached, wherein said ring optionally comprises an additional ring nitrogen. $R^2$ has the formula:

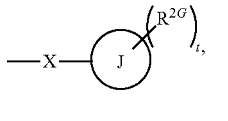

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$; J is phenyl; t is an integer from 0 to 5; X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, and $R^{5A1}$ is a member selected from hydrogen and unsubstituted alkyl, and $R^{5A2}$ and $R^{5A3}$ are members independently selected from hydrogen and unsubstituted alkyl, or salts and isomers thereof. Examples of such compounds are disclosed in U.S. Pat. Nos. 7,928,237 and 8,461,172, both of which patents are hereby incorporated by reference in their entireties.

In embodiments, the fused azadecalin SGRM is CORT108297, i.e., (R)-(4a-ethoxymethyl-1-(4-fluorophenyl)-6-(4-trifluoromethyl-benzenesulfonyl)-4,4a,5,6,7,8-hexahydro-1H,1,2,6-triaza-cyclopenta[b]naphthalene, which has the following structure:

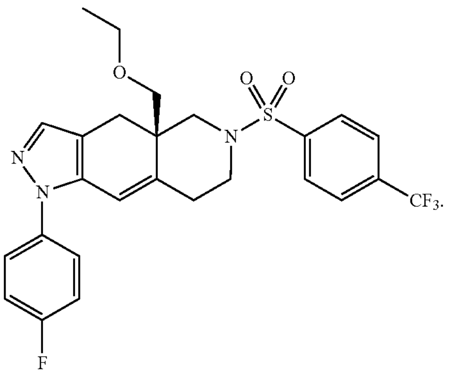 [SMILES: CCOC[C@]12Cc3cnn(-c4ccc(F)cc4)c3C=C1CCN(S(=O)(=O)c1ccc(C(F)(F)F)cc1)C2]

In some cases, the GRM backbone is a heteroaryl ketone fused azadecalin or an octahydro fused azadecalin. In some cases, the GRM having a heteroaryl ketone fused azadecalin or an octahydro fused azadecalin backbone is a SGRM, and may be a GRA or a SGRA.

Exemplary GRMs comprising a heteroaryl ketone fused azadecalin structure include those described in U.S. Pat. No. 8,859,774, which can be prepared as disclosed therein, and which is hereby incorporated herein in its entirety. Such exemplary GRMs may be SGRMs. In some cases, the GRM comprising a heteroaryl ketone fused azadecalin structure has the following structure:

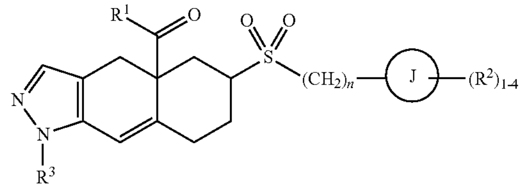

wherein

- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, and $C_{3-8}$ heterocycloalkyl;
- ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —C(O)$R^{2a}$, —C(O)$OR^{2a}$, —C(O)$NR^{2a}R^{2b}$, —$SR^{2a}$, —S(O)$R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^{2'}$ groups;
- alternatively, two $R^2$ groups linked to the same carbon are combined to form an oxo group (=O);
- alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;

each $R^{2d}$ is independently selected from the group consisting of hydrogen and $C_{1-6}$ alkyl, or two $R^{2d}$ groups attached to the same ring atom are combined to form (═O);

$R^3$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

or salts and isomers thereof.

In some cases, the heteroaryl-ketone fused azadecalin GRM is relacorilant (CORT125134), i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

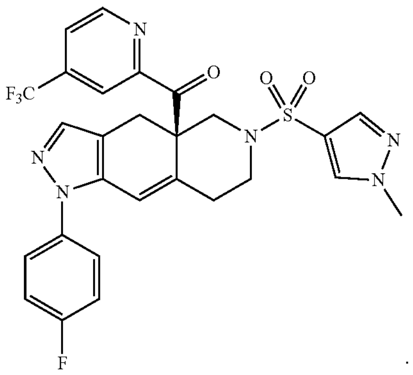 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

In embodiments, the heteroaryl-ketone fused azadecalin SGRM is the compound (R)-(1-(4-fluorophenyl)-6-((4-(trifluoromethyl)phenyl) sulfonyl)-4,4a, 5,6,7,8-hexahydro-1-H-pyrazolo P,4-g]isoquinolin-4a-yl) (pyridin-2-yl)methanone (termed “CORT113176”), which has the following structure:

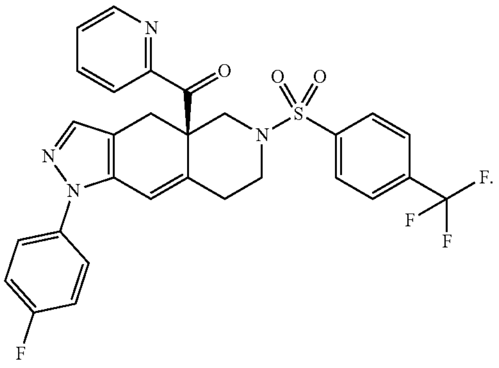 [SMILES: O=C(c1ccccn1)[C@]12Cc3cnn(-c4ccc(F)cc4)c3C=C1CCN(S(=O)(=O)c1ccc(C(F)(F)F)cc1)C2]

Exemplary GRMs comprising an octahydro fused azadecalin structure include compounds disclosed in U.S. Pat. No. 10,047,082, which is hereby incorporated by reference in its entirety. In embodiments, the octahydro fused azadecalin GRM has the formula:

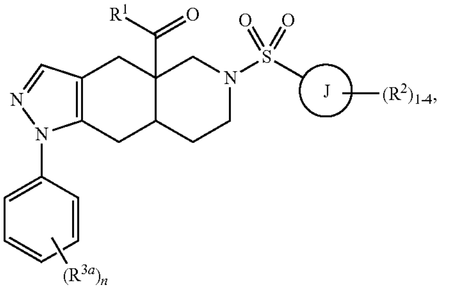

wherein $R^1$ is a heteroaryl ring having from 5 to 6 ring members and from 1 to 4 heteroatoms each independently selected from the group consisting of N, O, and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of an aryl ring and a heteroaryl ring having from 5 to 6 ring members and from 1 to 4 heteroatoms each independently selected from the group consisting of N, O, and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O, and S; alternatively, the two $R^2$ groups on adjacent ring atoms are combined to form a heterocycloalkyl ring having from 5 to 6 ring members and from 1 to 3 heteroatoms each independently selected from the group consisting of N, O, and S, wherein the heterocycloalkyl ring is optionally substituted with 1-3 $R^{2c}$ groups; $R^{2a}$, $R^{2b}$, and $R^{2c}$ are each independently selected from the group consisting of hydrogen and $C_{1-6}$ alkyl; each $R^{3a}$ is independently halogen; and subscript n is an integer from 0 to 3, or salts and isomers thereof.

In some cases, the octahydro fused azadecalin GRM is CORT125281, i.e., ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, which has the following structure:

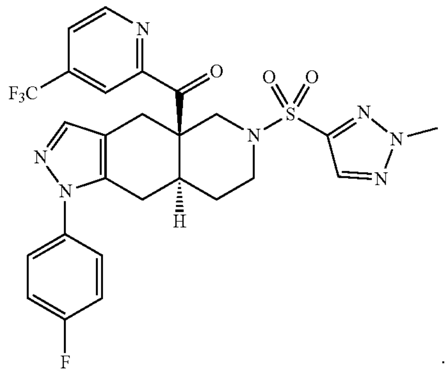 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

.

Identifying Selective Glucocorticoid Receptor Modulators (SGRMs)

To determine whether a test compound is a SGRM, the compound is first subjected to assays to measure its ability to bind to the GR and inhibit GR-mediated activities, which determines whether the compound is a glucocorticoid receptor modulator. The compound, if confirmed to be a glucocorticoid receptor modulator, is then subjected to a selectivity test to determine whether the compound can bind specifically to GR as compared to non GR proteins, such as the estrogen receptor, the progesterone receptor, the androgen receptor, or the mineralocorticoid receptor. In one embodiment, a SGRM binds to GR at a substantially higher affinity, e.g., at least 10 times higher affinity, than to non-GR proteins. A SGRM may exhibit a 100-fold, 1000-fold or greater selectivity for binding to GR relative to binding to non GR proteins.

Binding

A test compounds' ability to bind to the glucocorticoid receptor can be measured using a variety of assays, for example, by screening for the ability of the test compound to compete with a glucocorticoid receptor ligand, such as dexamethasone, for binding to the glucocorticoid receptor. Those of skill in the art will recognize that there are a number of ways to perform such competitive binding assays. In some embodiments, the glucocorticoid receptor is pre-incubated with a labeled glucocorticoid receptor ligand and then contacted with a test compound. This type of competitive binding assay may also be referred to herein as a binding displacement assay. A decrease of the quantity of labeled ligand bound to glucocorticoid receptor indicates that the test compound binds to the glucocorticoid receptor. In some cases, the labeled ligand is a fluorescently labeled compound (e.g., a fluorescently labeled steroid or steroid analog). Alternatively, the binding of a test compound to the glucocorticoid receptor can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Florida (1980); and "Practice and Theory of Enzyme Immunoassays," P. Tijssen, *Laboratory Techniques in Biochemistry and Molecular Biology*, Elsevier Science Publishers B. V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a glucocorticoid receptor ligand and the binding agent can be glucocorticoid receptor bound to a solid phase. Alternatively, the labeled analyte can be labeled glucocorticoid receptor and the binding agent can be a solid phase glucocorticoid receptor ligand. The concentration of labeled analyte bound to the capture agent is inversely proportional to the ability of a test compound to compete in the binding assay.

Alternatively, the competitive binding assay may be conducted in the liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the glucocorticoid receptor may be altered by the binding of the glucocorticoid receptor to its ligand or test compound. This alteration in the labeled glucocorticoid receptor results in a decrease or increase in the signal emitted by label, so that measurement of the label at the end of the binding assay allows for detection or quantitation of the glucocorticoid receptor in the bound state. A wide variety of labels may be used. The component may be labeled by any one of several methods. Useful radioactive labels include those incorporating $^{3}H$, $^{125}I$, $^{35}S$, $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art. In some cases, a test compound is contacted with a GR in the presence of a fluorescently labeled ligand (e.g., a steroid or steroid analog) with a known affinity for the GR, and the quantity of bound and free labeled ligand is estimated by measuring the fluorescence polarization of the labeled ligand.

HepG2 Tyrosine Aminotransferase (TAT) Assay

Compounds that have demonstrated the desired binding affinity to GR are tested for their activity in inhibiting GR mediated activities. The compounds are typically subject to a Tyrosine Aminotransferase Assay (TAT assay), which assesses the ability of a test compound to inhibit the induction of tyrosine aminotransferase activity by dexamethasone. See Example 1. GR modulators that are suitable for the method disclosed herein have an $IC_{50}$ (half maximal inhibition concentration) of less than 10 micromolar. Other assays, including but not limited to those described below, can also be deployed to confirm the GR modulation activity of the compounds.

Cell-Based Assays

Cell-based assays which involve whole cells or cell fractions containing glucocorticoid receptors can also be used to assay for a test compound's binding or modulation of activity of the glucocorticoid receptor. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemia cells, Burkitt's lymphoma cells, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, the glucocorticoid receptor can be expressed in cells that do not express an endogenous version of the glucocorticoid receptor.

In some cases, fragments of the glucocorticoid receptor, as well as protein fusions, can be used for screening. When molecules that compete for binding with the glucocorticoid receptor ligands are desired, the GR fragments used are fragments capable of binding the ligands (e.g., dexamethasone). Alternatively, any fragment of GR can be used as a target to identify molecules that bind the glucocorticoid receptor. Glucocorticoid receptor fragments can include any fragment of, e.g., at least 20, 30, 40, 50 amino acids up to a protein containing all but one amino acid of glucocorticoid receptor.

In some embodiments, a reduction in signaling triggered by glucocorticoid receptor activation is used to identify glucocorticoid receptor modulators. Signaling activity of the glucocorticoid receptor can be determined in many ways. For example, downstream molecular events can be monitored to determine signaling activity. Downstream events include those activities or manifestations that occur as a result of stimulation of a glucocorticoid receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g., the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Compounds that are tested in whole-cell assays can also be tested in a cytotoxicity assay. Cytotoxicity assays are used to determine the extent to which a perceived effect is due to non-glucocorticoid receptor binding cellular effects. In an exemplary embodiment, the cytotoxicity assay includes contacting a constitutively active cell with the test compound. Any decrease in cellular activity indicates a cytotoxic effect.

3) Additional Assays

Further illustrative of the many assays which can be used to identify compositions utilized in the methods of the invention, are assays based on glucocorticoid activities in vivo. For example, assays that assess the ability of a putative GR modulator to inhibit uptake of 3H-thymidine into DNA in cells which are stimulated by glucocorticoids can be used. Alternatively, the putative GR modulator can complete with 3H-dexamethasone for binding to a hepatoma tissue culture GR (see, e.g., Choi, et al., *Steroids* 57:313-318, 1992). As another example, the ability of a putative GR modulator to block nuclear binding of 3H-dexamethasone-GR complex can be used (Alexandrova et al., J. *Steroid Biochem. Mol. Biol.* 41:723-725, 1992). To further identify putative GR modulators, kinetic assays able to discriminate between glucocorticoid agonists and modulators by means of receptor-binding kinetics can also be used (as described in Jones, *Biochem J.* 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR modulator) at varying concentrations. $^{3}H$-uridine is added to the cell culture, which is further incubated, and the extent of incorporation of radiolabel into polynucleotide is measured. Glucocorticoid agonists decrease the amount of $^{3}H$-uridine incorporated. Thus, a GR modulator will oppose this effect.

iii. Selectivity

The GR modulators selected above are then subject to a selectivity assay to determine whether they are SGRMs. Typically, selectivity assays include testing a compound that binds glucocorticoid receptor in vitro for the degree of binding to non-glucocorticoid receptor proteins. Selectivity assays may be performed in vitro or in cell based systems, as described above. Binding may be tested against any appropriate non-glucocorticoid receptor protein, including antibodies, receptors, enzymes, and the like. In an exemplary embodiment, the non-glucocorticoid receptor binding protein is a cell-surface receptor or nuclear receptor. In another exemplary embodiment, the non-glucocorticoid receptor protein is a steroid receptor, such as estrogen receptor, progesterone receptor, androgen receptor, or mineralocorticoid receptor.

The selectivity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either a direct binding assay or by assessing competitive binding to the purified GR or MR in the presence of a known ligand. In an exemplary assay, cells that stably express the glucocorticoid receptor or mineralocorticoid receptor (see, e.g., U.S. Pat. No. 5,606, 021) at high levels are used as a source of purified receptor. The affinity of the ligand for the receptor is then directly measured. Those GR modulators that exhibit at least a 10 fold, 100-fold higher affinity, often 1000-fold, for the GR relative to the MR are then selected for use in the methods of the invention.

The selectivity assay may also include assaying the ability to inhibit GR-mediated activities, but not MR-mediated activities. One method of identifying such a GR-specific modulator is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or an analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. GR modulators that exhibits at least a 100-fold, often 1000-fold or greater, activity towards the GR relative to the MR, PR, or AR are then selected for use in the methods disclosed herein.

Pharmaceutical Compositions and Administration i. Formulations

In some embodiments, the present invention provides a pharmaceutical composition including a pharmaceutically acceptable excipient and a SGRM and a pharmaceutically acceptable excipient and a CIC or a CIA.

Any of the SGRMs, CICs, or CIAs disclosed herein can be formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

In embodiments, the present invention provides a pharmaceutical composition for treating patients suffering from ACC and having excess cortisol, the pharmaceutical composition including a pharmaceutically acceptable excipient and a GRM. In some embodiments, the pharmaceutical composition includes a pharmaceutically acceptable excipient and a SGRM. In preferred embodiments, the pharmaceutical composition includes a pharmaceutically acceptable excipient and a nonsterodial SGRM.

GRMs and SGRMs (as used herein, GRMs and SGRMs include nonsteroidal GRMs and nonsteroidal SGRMS), can be prepared and administered in a wide variety of oral, parenteral and topical dosage forms. Oral preparation s are preferred. Oral preparations include tablets, pills, powder, dragees, capsules, liquids, lozenges, gels, syrups, slurries, suspensions, etc., suitable for ingestion by the patient. GRMs and SGRMs can also be administered by injection, that is, intravenously, intramuscularly, intracutaneously, subcutaneously, intraduodenally, or intraperitoneally. Also, GRMs and SGRMs can be administered by inhalation, for example, intranasally. Additionally, GRMs and SGRMs can be administered transdermally. Accordingly, the present invention also provides pharmaceutical compositions including a pharmaceutically acceptable carrier or excipient and a GRM or SGRM.

For preparing pharmaceutical compositions from GRMs and SGRMs, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component, a GRM or SGRM. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a SGRM in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In embodiments, GRMs and SGRMs can be delivered by transdermally, by a topical route, formulated as applicator sticks, solutions, suspensions, emulsions, gels, creams, ointments, pastes, jellies, paints, powders, and aerosols.

GRMs and SGRMs can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component, a GRM or SGRM. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 6000 mg, most typically 50 mg to 500 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

GRMs, including SGRMs, can be administered orally. For example, the GRM can be administered as a pill, a capsule, or liquid formulation as described herein. Alternatively, GRMs can be provided via parenteral administration. For example, the GRM can be administered intravenously (e.g., by injection or infusion). Additional methods of administration of the compounds described herein, and pharmaceutical compositions or formulations thereof, are described herein.

In some embodiments, the GRM is administered in one dose. In other embodiments, the GRM is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount will vary according to, for example, the GRM properties and patient characteristics.

Any suitable GRM dose may be used in the methods disclosed herein. The dose of GRM that is administered can be at least about, e.g., 100 milligrams (mg) per day, about 150 mg/day, about 200 mg/day, about 250 mg/day, about 300 mg/day, about 350 mg/day, about 400 mg/day, about 450 mg/day, about 500 mg/day, about 550 mg/day, about 600 mg/day, about 650 mg/day, about 700 mg/day, about 750 mg/day, about 800 mg/day, about 850 mg/day, about 900 mg/day, about 950 mg/day, about 1000 mg/day, or more.

In some cases, the effective amount of the GRM (e.g., a SGRM, such as a nonsteroidal SGRM) is a daily dose of between 1 and 30 mg/kg/day, wherein the GRM is administered with at least one chemotherapeutic agent. In some embodiments, the daily dose of the GRM is 1, 2, 4, 6, 8, 10, 12, 14, 16, 18, 20, 22, 24, 25, or 30 mg/kg/day. In some cases, the GRM is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

In embodiments, the GRM is administered orally. In some embodiments, the GRM is administered in at least one dose. In other words, the GRM can be administered in 1, 2, 3, 4, 5, 6, 7, 8, 9, 10 or more doses. In embodiments, the GRM is administered orally in 1, 2, 3, 4, 5, 6, 7, 8, 9, 10 or more doses.

The subject may be administered at least one dose of GRM in one or more doses over, for example, a 2-48 hour period. In some embodiments, the GRM is administered as a single dose. In other embodiments, the GRM is administered in more than one dose, e.g. 2 doses, 3 doses, 4 doses, 5 doses, or more doses over a 2-48 hour period, e.g., a 2 hour period, a 3 hour period, a 4 hour period, a 5 hour period, a 6 hour period, a 7 hour period, a 8 hour period, a 9 hour period, a 10 hour period, a 11 hour period, a 12 hour period, a 14 hour period, a 16 hour period, a 18 hour period, a 20 hour period, a 22 hour period, a 24 hour period, a 26 hour period, a 28 hour period, a 30 hour period, a 32 hour period, a 34 hour period, a 36 hour period, a 38 hour period, a 40 hour period, a 42 hour period, a 44 hour period, a 46 hour period or a 48 hour period. In some embodiments, the GRM is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

Single or multiple administrations of formulations can be administered depending on the dosage and frequency as required and tolerated by the patient. The formulations should provide a sufficient quantity of active agent to effectively treat the disease state. Thus, in one embodiment, the pharmaceutical formulation for oral administration of a GRM is in a daily amount of between about 0.01 to about 150 mg per kilogram of body weight per day (mg/kg/day). In some embodiments, the daily amount is from about 1.0 to 100 mg/kg/day, 5 to 50 mg/kg/day, 10 to 30 mg/kg/day, and 10 to 20 mg/kg/day. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

The duration of treatment with a GRM or SGRM to treat ACC in patients having excess cortisol can vary according to the severity of the condition in a subject and the subject's response to GRMs or SGRMs. In some embodiments, GRMs and SGRMs can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. Generally administration of a GRM or SGRM should be continued until clinically significant reduction or amelioration is observed. Treatment with the GRM or SGRM in accordance with the invention may last for as long as two years or even longer.

In some embodiments, administration of a GRM or SGRM is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

In addition, SGRMs can be used in combination with other active agents known to be useful in modulating a glucocorticoid receptor, or with adjunctive agents that may not be effective alone, but may contribute to the efficacy of the active agent. The novel methods disclosed herein include administration of a SGRM in combination with an antibody checkpoint inhibitor.

In some embodiments, co-administration includes administering one active agent, a GRM or SGRM, within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a SGRM has been formulated in an acceptable carrier, it can be placed in an appropriate container and labeled for treatment of an indicated condition. For administration of a GRM or SGRM, such labeling would include, e.g., instructions concerning the amount, frequency and method of administration.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

ii. Dosage

Pharmaceutical compositions suitable for administration include compositions, where the active ingredients, e.g., checkpoint inhibitors and SGRMs are contained in an amount effective to achieve their intended purpose. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compositions of the present invention employed, or the ester, salt or amide thereof, the pharmacokinetics of the composition, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical compositions of the invention are preferably in unit dosage form. In such form the preparation is subdivided into unit doses containing appropriate quantities of the active component, a GRM (e.g., a SGRM) or an antibody checkpoint inhibitor. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The dosage regimen of the checkpoint inhibitors or the GRMs (e.g., SGRMs) also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, SGRM and the checkpoint inhibitor based on the disease or condition treated.

The quantity of active component in a unit dose preparation may be varied or adjusted from 0.1 mg to 6000 mg, more typically 1.0 mg to 3000 mg, most typically 10 mg to 300 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents. Single or multiple administrations of compositions can be administered depending on the dosage and frequency as required and tolerated by the patient.

The compositions containing an antibody checkpoint inhibitor should provide a sufficient quantity of the active component, i.e., the antibody checkpoint inhibitor, when administered alone or in combination with a GRM (e.g., SGRM), to effectively treat the cancer, for example, in an amount being able to reduce ACC tumor load or achieve other beneficial or desired clinical results related to cancer improvement. Thus, the dosage regimen may vary widely, but can be determined routinely using standard methods. In some cases, the pharmaceutical composition comprises a CIC and administration of a daily dose of about 1 to 2,000 mg, preferably between about 10 and about 1000 mg and most preferably between about 250 to 500 mg of the active ingredient, may be appropriate. The daily dose can be administered in one to four doses per day. Other dosing schedules include one dose per week and one dose per two-day cycle.

In some cases, the pharmaceutical compositions contain a CIA, and the dosage (of the active component) ranges from about 0.0001 to 100 mg/kg, and more usually 0.01 to 20 mg/kg, of the host body weight. For example dosages can be 0.3 mg/kg body weight, 1 mg/kg body weight, 3 mg/kg body weight, 5 mg/kg body weight, 10 mg/kg body weight or within the range of 0.1-20 mg/kg. An exemplary treatment regime entails administration once per day, once per week, twice a week, once every two weeks, once every three weeks, once every four weeks, once a month, once every 3 months or once every three to 6 months. In some cases, the treatment comprises administering a CIA according one of the aforementioned dosing regimens for a first period and another of the aforementioned dosing regimens for a second period. In some cases, the treatment discontinues for a period of time before the same or a different dosing regimen resumes. For example, a patient may be on a CIA dosing regimen for two weeks, off for a week, on for another two weeks, and so on. Preferred dosage regimens for a CIA of the invention include 0.1 mg/kg body weight, 0.3 mg/kg body weight, 2 mg/kg body weight, 3 mg/kg body weight or 10 mg/kg via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks In some methods, two or more CIAs with different binding specificities are administered simultaneously, in which case the dosage of each antibody administered falls within the ranges indicated. CIAs are usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

The compositions containing a GRM (e.g., a SGRM) used in the combination therapy should provide a sufficient quantity of active agent to effectively potentiate the activity of the checkpoint inhibitor in treating cancer, for example, in an amount that, when combined with the therapeutic amount of an antibody checkpoint inhibitor, can reduce ACC tumor load, restore T-cell and natural killer (NK) cell signaling pathways, increase T-cell and NK cell infiltration into the ACC tumor, reduce neutrophil infiltration into the ACC tumor in the patient, or otherwise alleviate related cancer symptoms to a greater degree, or achieve greater beneficial or desired clinical results, as compared to the administration of the checkpoint inhibitor in the same therapeutic amount without the GRM (e.g., a SGRM). In some cases, the compositions provide a GRM (e.g., SGRM) at an amount that renders the ACC tumor sensitive to the checkpoint inhibitor, i.e., a showing of a reduction of tumor load or other related clinical benefit that would not otherwise appear when the tumor is treated with the checkpoint inhibitor alone. Thus, the dosage regimen may vary widely, depending on the route of administration and type of cancers to be treated, but can be determined routinely using standard methods. In some embodiments, the GRM (e.g., the SGRM) is administered once per month, twice per month, three times per month, every other week, once per week, twice per week, three times per week, four times per week, five times per week, six times per week, every other day, daily, twice a day, three times a day or more frequent, In some cases, the daily oral dosage for the pharmaceutical composition containing a GRM (e.g., a SGRM) can be used for the methods disclosed herein, ranges from about 1 to about 2000 mg per day (mg/day). In some embodiments, the daily amount is from about 10 to 1000 mg/day, 50 to 500 mg/day, 100 to 300 mg/day. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable compositions will be known or apparent to those skilled in the art and are described in more detail in such publications as Remington's, supra. See also Nieman, In "Receptor Mediated Antisteroid Action," Agarwal, et al., eds., De Gruyter, New York (1987). In some embodiments, the SGRM is CORT125281. In some embodiments, the SGRM is CORT 125134.

After a pharmaceutical composition including a GRM (e.g., a SGRM) or an antibody checkpoint inhibitor of the invention has been formulated in an acceptable carrier, it can be placed in an appropriate container and labeled for treatment of an indicated condition. For administration of a GRM (e.g., a SGRM) or checkpoint inhibitor, such labeling would include, e.g., instructions concerning the amount, frequency and method of administration.

Combination Therapy

The method disclosed herein involves a combination therapy of administering both a GRM (e.g., a SGRM) and an antibody checkpoint inhibitor to a subject that suffers from a ACC tumor load, which, in some cases, is due to the presence of an antibody checkpoint inhibitor sensitive cancer. In some embodiments, the combination therapy involves administration of an antibody checkpoint inhibitor and a SGRM sequentially in any order during the entire or portions of the treatment period. The combination therapy comprising administration of both a GRM (e.g., a SGRM) and an antibody checkpoint inhibitor to a subject that suffers from a ACC tumor load, is believed to be effective to reduce ACC tumor load, restore T-cell and natural killer (NK) cell signaling pathways, increase T-cell and NK cell infiltration into the ACC tumor, reduce neutrophil infiltration into the ACC tumor in the patient, and provide other therapeutic benefits to the patient.

In some cases, the GRM (e.g., a SGRM) and the checkpoint inhibitor are administered following the same or different dosing regimen. In some cases, the GRM (e.g., a SGRM) is administered following a scheduled regimen while the checkpoint inhibitor is administered intermittently. In some cases, the checkpoint inhibitor is administered following a scheduled regimen while the GRM (e.g., a SGRM) is administered intermittently. In some cases, both the GRM (e.g., a SGRM) and the checkpoint inhibitor are administered intermittently. In some embodiments, the GRM (e.g., a SGRM) is administered daily, and the checkpoint inhibitor, e.g., an antibody checkpoint inhibitor, is administered weekly or biweekly.

In some cases, the GRM (e.g., a SGRM) and the checkpoint inhibitor are administered sequentially or simultaneously once or twice per month, three times per month, every other week, once per week, twice per week, three times per week, four times per week, five times per week, six times per week, every other day, daily, twice a day, three times a day or more frequent, continuously over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments, the combination therapy includes co-administering a GRM (e.g., a SGRM) and an antibody checkpoint inhibitor. In some embodiments, co-administration of an antibody checkpoint inhibitor and a GRM (e.g., a SGRM) involves administering the two agents simultaneously or approximately simultaneously (e.g., within about 1, 5, 10, 15, 20, or 30 minutes of each other).

Various combinations with a GRM or SGRM and an antibody checkpoint inhibitor may be employed to treat the patient suffering from an ACC and having excess cortisol. Such treatment may be effective to reduce the ACC tumor load, restore T-cell and natural killer (NK) cell signaling pathways, increase T-cell and NK cell infiltration into the ACC tumor, reduce neutrophil infiltration into the ACC tumor in the patient, and provide other therapeutic benefits to the patient. By "combination therapy" or "in combination with", it is not intended to imply that the therapeutic agents must be administered at the same time and/or formulated for delivery together, although these methods of delivery are within the scope described herein. The GRM or SGRM and the antibody checkpoint inhibitor can be administered following the same or different dosing regimen. In some embodiments, the GRM or SGRM and the antibody checkpoint inhibitor are administered sequentially in any order during the entire or portions of the treatment period. In some embodiments, the GRM or SGRM and the antibody checkpoint inhibitor are administered simultaneously or approximately simultaneously (e.g., within about 1, 5, 10, 15, 20, or 30 minutes of each other). Non-limiting examples of combination therapies are as follows, with administration of the GRM or SGRM and the antibody checkpoint inhibitor for example, GRM or SGRM is "A" and the antibody checkpoint inhibitor, given as part of an chemo therapy regime, is "B":

| | | | | | | |
|---|---|---|---|---|---|---|
| A/B/AB/A/BB/B/AA/A/BA/B/BB/A/AA/B/B/B | B/A/B/B | | | | | |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

Administration of the therapeutic compounds or agents to a patient will follow general protocols for the administration of such compounds, taking into account the toxicity, if any, of the therapy. Surgical intervention may also be applied in combination with the described therapy.

The present methods can be combined with other means of treatment such as surgery, radiation, targeted therapy, immunotherapy, use of growth factor inhibitors, or anti-angiogenesis factors.

Duration

The duration of treatment with a GRM (e.g., a SGRM) and an antibody checkpoint inhibitor to reduce tumor load, restore T-cell and natural killer (NK) cell signaling pathways, increase T-cell and NK cell infiltration into the ACC tumor, reduce neutrophil infiltration into the ACC tumor in the patient, and to provide other therapeutic benefits to the patient can vary according to the severity of the condition in a subject and the subject's response to the combination therapy. In some embodiments, the GRM (e.g., the SGRM) and/or the checkpoint inhibitor can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. Generally, administration of a SGRM and/or an antibody checkpoint inhibitor should be continued until the desired clinical benefit is observed, and may be continued after such benefit is observed, e.g., to maintain or to further enhance such benefit. Treatment with a GRM (e.g., a SGRM) and an antibody checkpoint inhibitor in accordance with the invention may last for as long as two years or even longer. In some embodiments, the duration of the GRM (e.g., a SGRM) administration is the same as that of the checkpoint inhibitor. In some embodiments, the duration of SGRM administration is shorter or longer than that of the checkpoint inhibitor.

In some embodiments, administration of a GRM (e.g., a SGRM) or an antibody checkpoint inhibitor is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

Evaluate Improvements in Treating ACC in Patients with Excess Cortisol, Including Reducing Tumor Loads The combination therapy disclosed herein is believed to be effective to treat patients having excess cortisol and suffering from an ACC tumor; in embodiments, such treatment may be effective to reduce tumor load in the patient, to restore T-cell and natural killer (NK) cell signaling pathways, to increase T-cell and NK cell infiltration into the ACC tumor, to reduce neutrophil infiltration into the ACC tumor in the patient, and to provide other therapeutic benefits to the patient. Methods for measuring these responses are well-known to skilled artisans in the field of cancer therapy. For example, methods for measuring tumor load are described in the Response Evaluation Criteria in Solid Tumors ("RECIST") guidelines, available at http://ctep.cancer.gov/protocolDevelopment/docs/recist_guideline.pdf.

In one approach, the tumor load is measured by assaying expression of tumor-specific genetic markers. This approach is especially useful for metastatic tumors or tumors that are not easily measurable, e.g., bone marrow cancer. A tumor-specific genetic marker is a protein or other molecule that is unique to cancer cells or is much more abundant in them as compared to non-cancer cells. For example, see WO 2006104474. Non-limiting examples of tumor-specific genetic markers include, alpha-fetoprotein (AFP) for liver cancer, beta-2-microglobulin (B2M) for multiple myeloma; beta-human chorionic gonadotropin (beta-hCG) for choriocarcinoma and germ cell tumors; CA19-9 for pancreatic cancer, gall bladder cancer, bile duct cancer, and gastric cancer; CA-125 and HE4 for ovarian cancer; carcinoembryonic antigen (CEA) for colorectal cancer; chromogranin A (CgA) for neuroendocrine tumor; fibrin/fibrinogen for bladder cancer; prostate-specific antigen (PSA) for prostate cancer; and thyroglobulin for thyroid cancer. See, http://www.cancer.gov/about-cancer/diagnosis-staging/diagnosis/tumor-markers-fact-sheet.

Methods of measuring the expression levels of a tumor-specific genetic marker are well known. In some embodiments, mRNA of the genentic marker is isolated from the blood sample or a tumor tissue and real-time reverse transcriptase-polymerase chain reaction (RT-PCR) is performed to quantify expression of the genetic marker. In some embodiments, western blots or immunohistochemistry analysis are performed to evaluate the protein expression of the tumor-specific genetic marker. Typically the levels of the tumor-specific genetic marker are measured in multiple samples taken over time of the combination therapy of the invention, and a decrease in levels correlates with a reduction in tumor load.

In another approach, the reduction of tumor load by the combination therapy disclosed herein is shown by a reduction in tumor size or a reduction of amount of cancer in the body. Measuring tumor size is typically achieved by imaging-based techniques. For example, computed tomography (CT) scan can provide accurate and reliable anatomic information about not only tumor shrinkage or growth but also progression of disease by identifying either growth in existing lesions or the development of new lesions or tumor metastasis. Restoration of T-cell and natural killer (NK) cell signaling pathways, increase in T-cell and NK cell infiltration into the ACC tumor, and reduction of neutrophil infiltration into the ACC tumor in the patient may also be measured by image-based techniques, or other suitable means.

In another approach, a reduction of tumor load, restoration of T-cell and natural killer (NK) cell signaling pathways, increase in T-cell and NK cell infiltration into the ACC tumor, and reduction of neutrophil infiltration into the ACC tumor in the patient may be assessed by functional and metabolic imaging techniques. These techniques can provide earlier assessment of therapy response by observing alterations in perfusion, oxygenation and metabolism. For example, $^{18}$F-FDG PET uses radiolabelled glucose analogue molecules to assess tissue metabolism. Tumors typically have an elevated uptake of glucose, a change in value corresponding to a decrease in tumor tissue metabolism indicates a reduction in tumor load. Similar imaging techniques are disclosed in Kang et al., Korean J. Radiol. (2012) 13(4) 371-390.

A patient receiving the combination therapy disclosed herein may exhibit varying degrees of tumor load reduction, and may exhibit varying degrees of restoration of T-cell and natural killer (NK) cell signaling pathways, increase in T-cell and NK cell infiltration into the ACC tumor, and reduction of neutrophil infiltration into the ACC tumor in the patient. In some cases, a patient can exhibit a Complete Response (CR), also referred to as "no evidence of disease (NED)". CR means all detectable tumor has disappeared as indicated by tests, physical exams and scans. In some cases, a patient receiving the combination therapy disclosed herein can experience a Partial Response (PR), which roughly corresponds to at least a 50% decrease in the total tumor volume but with evidence of some residual disease still remaining. In some cases the residual disease in a deep partial response may actually be dead tumor or scar so that a few patients classified as having a PR may actually have a CR. Also many patients who show shrinkage during treatment show further shrinkage with continued treatment and may achieve a CR. In some cases, a patient receiving the combination therapy can experience a Minor Response (MR), which roughly means a small amount of shrinkage that is more than 25% of total tumor volume but less than the 50% that would make it a PR. In some cases, a patient receiving the combination therapy can exhibit Stable Disease (SD), which means the tumors stay roughly the same size, but can include either a small amount of growth (typically less than 20 or 25%) or a small amount of shrinkage (Anything less than a PR unless minor responses are broken out. If so, then SD is defined as typically less 25%).

In addition to reduction in ACC tumor load, restoration of T-cell and natural killer (NK) cell signaling pathways, increase in T-cell and NK cell infiltration into the ACC tumor, and reduction of neutrophil infiltration into the ACC tumor, desired beneficial or desired clinical results from the combination therapy may also include e.g., reduced (i.e., slowing to some extent and/or stop) cancer cell infiltration into peripheral organs; inhibit (i.e., slow to some extent and/or stop) tumor metastasis; increased response rates (RR); increased duration of response; relieved to some extent one or more of the symptoms associated with the cancer; decreased dose of other medications required to treat the disease; delayed progression of the disease; and/or prolonged survival of patients and/or improved quality of life. Methods for evaluating these effects are well known and/or disclosed in, e.g., http://cancerguide.org/endpoints.html and RECIST guidelines, supra.

EXAMPLES

The following examples are provided by way of illustration only and not by way of limitation. Those of skill will readily recognize a variety of noncritical parameters which could be changed or modified to yield essentially similar results.

Example 1. HepG2 Tyrosine Aminotransferase (Tat) Assay

The following protocol describes an assay for measuring induction of TAT by dexamethasone in HepG2 cells (a human liver hepatocellular carcinoma cell line; ECACC, UK). HepG2 cells are cultured using MEME media supplemented with 10% (v/v) foetal bovine serum; 2 mM L-glutamine and 1% (v/v) NEAA at 37° C., 5%/95% (v/v) $CO_2$/air. The HepG2 cells are then be counted and adjusted to yield a density of $0.125\times10^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% $CO_2$ for 24 hours.

Growth media are then removed and replaced with assay media {RPMI 1640 without phenol red, 2 mM L-glutamine+10 µM forskolin}. Test compounds are then screened against a challenge of 100 nM dexamethasone. Compounds are then be serially half log diluted in 100% (v/v) dimethylsupfoxide from a 10 mM stock. Then an 8-point half-log dilution curve are generated followed by a 1:100 dilution into assay media to give a 10× final assay of the compound concentration, this results in final assay of the compound concentration that ranged 10 to 0.003 µM in 0.1% (v/v) dimethylsulfoxide.

Test compounds are pre-incubated with cells in micro-titre plates for 30 minutes at 37° C., 5/95 (v/v) $CO_2$/air, before the addition of 100 nM dexamethasone and then subsequently for 20 hours to allow optimal TAT induction.

HepG2 cells are then lysed with 30 µl of cell lysis buffer containing a protease inhibitor cocktail for 15 minutes at 4° C. 155 µl of substrate mixture can then be added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction can be terminated by the addition of 15 µl of 10M aqueous potassium hydroxide solution, and the plates incubated for a further 30 minutes at 37° C. The TAT activity product can be measured by absorbance at X, 340 nm.

$IC_{50}$ values can be calculated by plotting % inhibition (normalised to 100 nM dexamethasone TAT stimulation) v. compound concentration and fitting the data to a 4 parameter logistic equation. $IC_{50}$ values can converted to Ki (equilibrium dissociation constant) using the Cheng and Prusoff equation, assuming the antagonists were competitive inhibitors with respect to dexamethasone.

Example 2. Gene Expression in ACC Tumor Patients with Cortisol Excess

Methods: GC status, mRNA expression, DNA mutation, and DNA methylation data from distinct adrenal resections (n=71) were accessed via The Cancer Genome Atlas (TCGA) (accessible via the "cancer.gov" URL at about-nci/organization/ccg/research/structural-genomics/tcga). To deconvolute immune cell type abundance, xCell was applied to the mRNA data. Random forest was used to derive gene signatures (Aran, Dvir, Zicheng Hu, and Atul J. Butte. "xCell: digitally portraying the tissue cellular heterogeneity landscape." *Genome biology* 18.1 (2017): 220). Gene analysis may also be performed via the cBioPortal (accessible via cbioportal.org).

Results: The expression of 858 genes differed significantly between GC− and GC+ ACC cases. KEGG pathway analysis showed higher gene expression of 7 pathways involved in steroid synthesis and secretion in GC+ cases. Nineteen pathways showed lower expression, most of which were related to natural killer cells, T-cells, and immune activity. Hypomethylation was primarily observed in the steroid synthesis pathways. Tumor-infiltrating $CD4^+$ memory (P=0.003), $CD8^+$ memory (P<0.001), and NKT-cells (P=0.014) were depleted in GC+ cases, while tumor-associated neutrophils were enriched (P<0.001). Higher tumor mutation burden (TMB) was observed in the GC+ cases (P=0.029).

GC+ ACC tumors exhibited specific differences in immune processes as compared to ACC tumors without systemic cortisol excess. Specifically, genes involved in natural killer (NK) mediated cytotoxicity, $T_H17$ cell differentiation, T cell receptor signaling, $T_H1/2$ differentiation, and antigen processing and presentation were downregulated in GC+ ACC tumors (FIG. 1).

Figure 2:
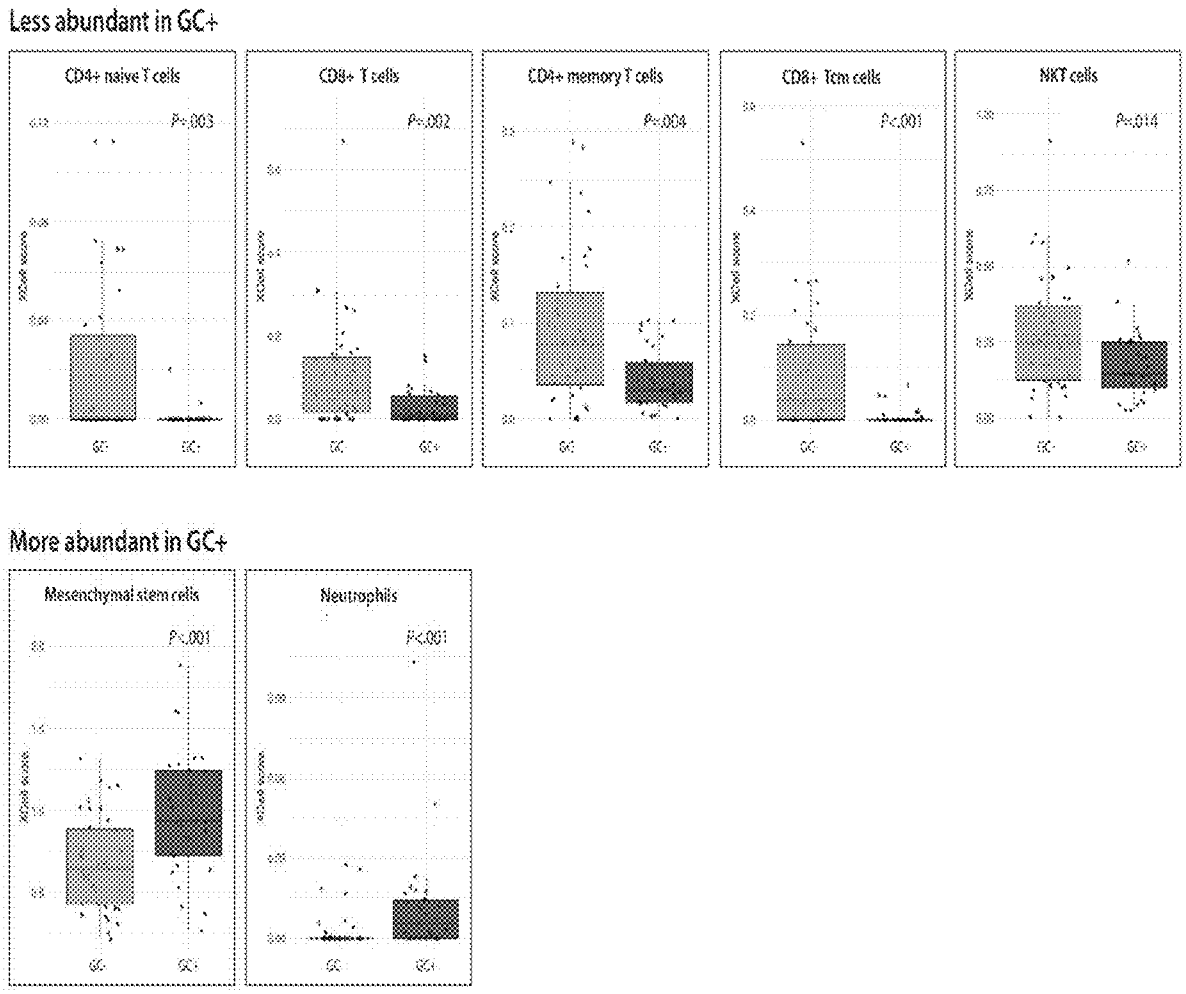
FIG. 2 shows the abundance of specific immune cell types in ACC tumors. Lymphocyte abundance was lower (left), while mesenchymal stem cells and neutrophil abundance was higher (right) in GC+ cases.

Further, the presence of specific immune cells was different in ACC tumors with or without cortisol excess. Naïve and memory CD4+ cells, CD8+ cells, CD8+ central memory cells, and natural killer T-cells (NKT)s were lower in GC+ cases (FIG. 2). In contrast, tumor associated neutrophils (TAN) were higher in GC+ ACC.

The abundance of immune cells and immune-related transcripts is lower in GC+ ACC. Higher TMB in GC+ tumors may be related to increased tolerance to neoantigens. These findings suggest that GR antagonism may promote the tumor immune response in ACC, or other malignancies with elevated GC activity, by reversing immunosuppressive effects of endogenous GC.

CONCLUSIONS

Clinical response to antibody checkpoint inhibitors is dependent on the immune system. Specifically, T-cell function and antigen presentation are critical for clinical efficacy of antibody checkpoint inhibitors. Further, infiltration of immune cells is associated with clinical efficacy of antibody checkpoint inhibitors. Tumors with low T-cell or high neutrophil infiltration tend to have poor responses to antibody checkpoint inhibitors. Thus, reversing the effects of GC+ using a GRM (e.g., a SGRM) may improve response to antibody checkpoint inhibitor. Thus, it is believed that administration of a GRM, such as a SGRM, in combination with an antibody checkpoint inhibitor is effective to reduce tumor load, restore T-cell and natural killer (NK) cell signaling pathways, increase T-cell and NK cell infiltration into the ACC tumor, reduce neutrophil infiltration into the ACC tumor in a patient suffering from ACC and having cortisol excess.

Example 3. Gene Expression in ACC Tumor Patients with Cortisol Excess

Methods: GC status (based on clinical signs and symptoms or biochemical evidence), mRNA expression, DNA mutation, and DNA methylation data from distinct adrenal resections (n=71) were accessed via TCGA (www.cancer-.gov/tcga). Two sarcomatoid cases were excluded from the analysis. 394,036 methylation probes were analyzed, and data were normalized using beta-mixture quantile normalization (BMIQ). To deconvolute immune cell type abundance, xCell was applied to the mRNA data (Aran et al., *Genome Biol.* 18(1):220 (2017)). Tumor cases were scored using a published GR activity signature (West et al., 24(14): 3433-3446 (2018)). Random forests were used to derive a gene signature predictive of GC+ tumors. Signature genes were identified by bootstrapping random forests on random subsets comprising 80% of the data and comparing the mean bootstrapped importance of genes with a threshold value. The threshold value was calculated by applying the same procedure to a random forest predicting randomized labels instead of the true GC+/− labels to simulate lack of signal. The 99.9-th quantile of gene importance was selected as the threshold.

Figure 3A:
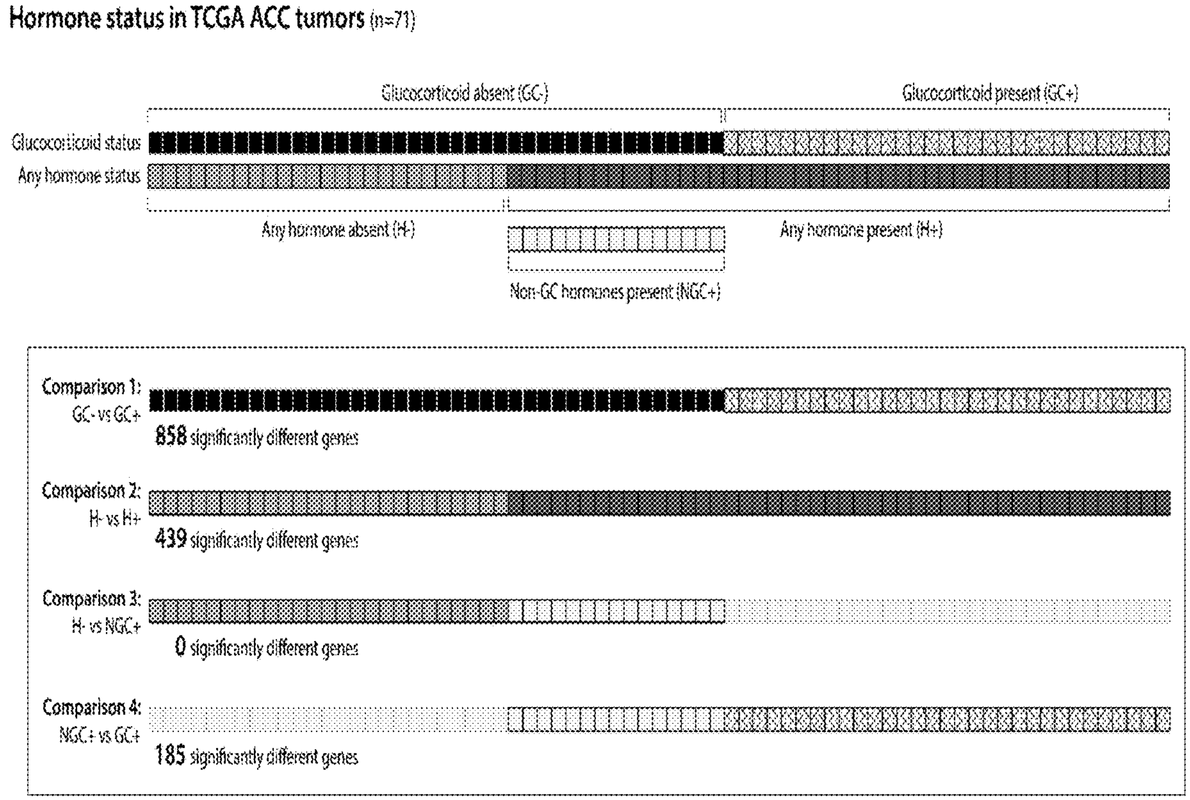
FIG. 3A. Classification of ACC Tumors by Hormone Status. Among the 4 comparisons performed, presence or absence of GC excess (GC+/−) was associated with the largest number of significantly different genes in ACC (where "GC-" indicates ACC patients not exhibiting GC excess).

Results: Adrenocortical carcinomas were classified using glucocorticoid status of the tumor. (FIG. 3A) Using mRNA data in TCGA, genes that differed significantly by general hormone or GC status (>2-fold change and adjusted P<0.05) were identified. The presence or absence of GC excess (GC+/−) was identified as affecting the largest number of genes (858 genes, comparison 1 in FIG. 3A, and as shown 3B). Determination of the presence vs absence of any hormone (H+/−) led to a significant difference in 439 genes (Comparison 2). (H+ indicates the presence of a hormone, and H− indicates the absence of a hormone (e.g., no GC, androgen, estrogen, progesterone, etc. were detected.)) There was no significant difference between H− tumors and those expressing only non-GC hormones (NGC+, Comparison 3). A comparison of NGC+ vs GC+ revealed 185 significantly different genes (Comparison 4). Kyoto Encyclopedia of Genes and Genomes (KEGG) pathway analysis identified higher gene expression in GC+ cases in several steroid-synthesis pathways and lower expression in a number of immune-related pathways (FIG. 1).

As noted in Example 2 above, FIG. 2 shows the abundance of specific immune cell types in ACC tumors. Lymphocyte abundance was lower (left), while mesenchymal stem cells and neutrophil abundance was higher (right) in GC+ cases. GC+ ACC tumors show lower lymphocyte abundance, higher myeloid and mesenchymal stem cell abundance, and higher tumor mutation burden. xCell analysis showed that T cells (P<0.005) and natural killer T cells (NKT cells, P=0.014) were less abundant in GC+ cases compared to GC− (FIG. 2, left). In contrast, mesenchymal stem cells and neutrophils were more abundant in GC+ cases (P<0.001, FIG. 2, right). Higher tumor mutation burden was also observed in the GC+ cases (P=0.029, FIG. 7).

Figure 3B:
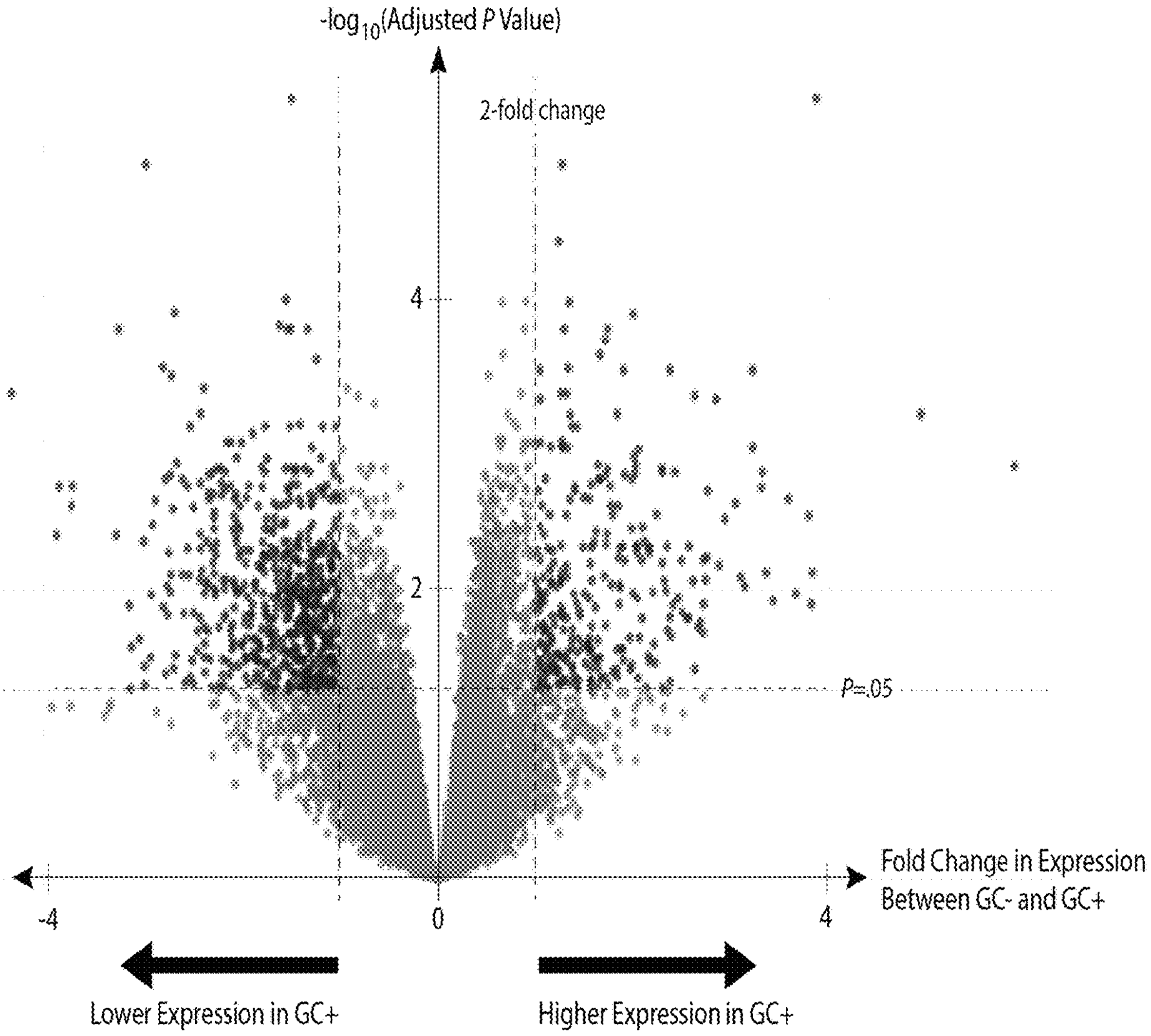
FIG. 3B Transcriptional Effects of GC Excess. Expression of 858 genes was found to be significantly affected by GC excess. Genes with higher expression in GC+ cases ($P \leq 0.05$ and >2-fold change in expression compared to GC−) are shown on the right. Those with lower expression in GC+ cases are shown on the left.

As shown in FIG. 3B, the expression of 858 genes was found to be significantly affected by GC excess. Genes with higher expression in GC+ cases (P<0.05 and >2-fold change in expression compared to GC−) are shown on the upper right. Those with lower expression in GC+ cases are shown on the upper left.

Figure 4:
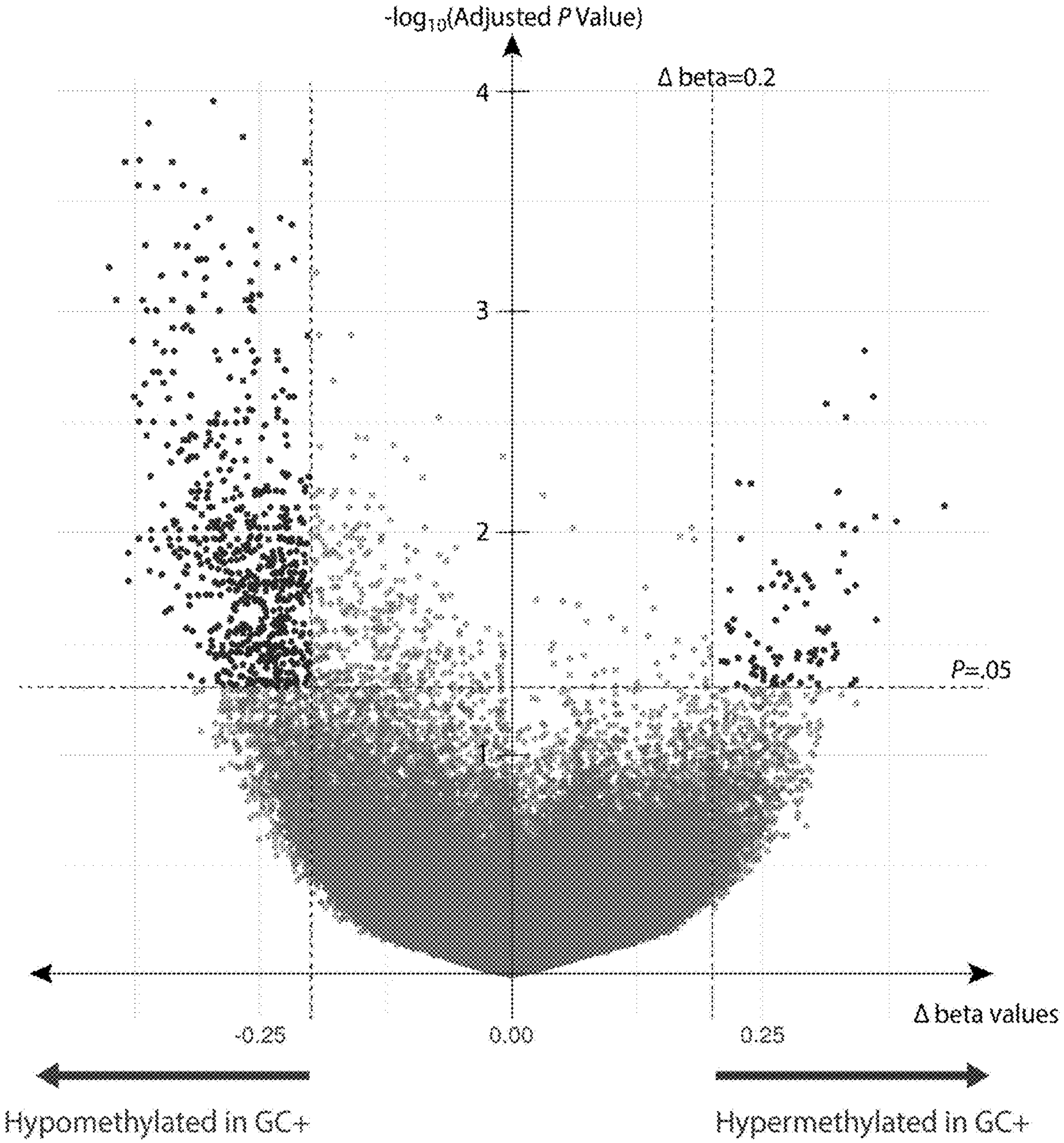
FIG. 4. Effects of GC on Promoter Methylation. More genes were significantly hypomethylated ($P \leq 0.05$, $\Delta$ beta<−0.2) than hypermethylated ($P \leq 0.05$, $\Delta$ beta>0.2) in GC+ tumors. Beta values represent the percentage of methylation in a gene.

GC excess is associated with hypomethylation of steroid synthesis genes (FIG. 4). In GC+ ACC cases, a large number of genes were significantly hypomethylated (FIG. 4, upper left), while fewer genes were hypermethylated (FIG. 4, upper right). More genes were significantly hypomethylated (P<0.05, A beta<−0.2) than hypermethylated (i=0.05, A beta>0.2) in GC+ tumors (FIG. 4). Beta values represent the percentage of methylation in a gene. Differences in methylation may explain the upregulation of steroidogenesis pathways but not the downregulation of immune pathways. The hypomethylated genes were primarily associated with aldosterone, GC, and bile synthesis/secretion—pathways that are upregulated in GC+ ACC (FIG. 1). In contrast, the immune pathways with downregulated gene expression identified by mRNA analysis were not enriched in either the hypo- or hypermethylated sets.

Figure 5:
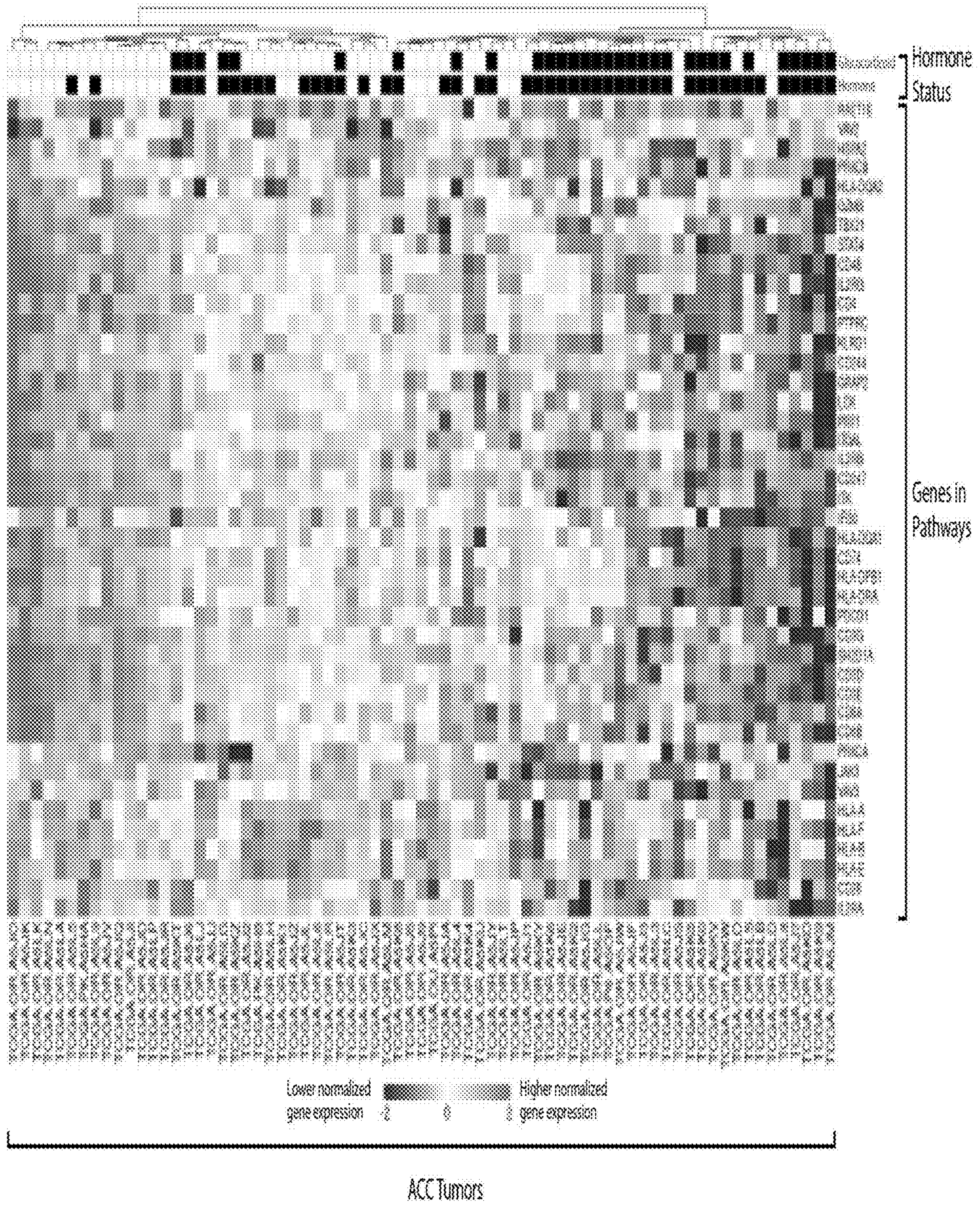
FIG. 5. Unsupervised Clustering of Normalized Gene Expression for 2 KEGG Pathways. Pathways shown include T-cell receptor signaling and natural-killer-cell-mediated cytotoxicity. The top 2 rows indicate GC and general hormone status for each tumor (black: GC+/H+, white: GC−/H−), shades of blue/red (shown in greyscale) show normalized gene expression for each tumor, with darker blue corresponding to lower expression. When clustering by gene expression, GC+ cases appear toward the right of the figure, where many genes show lower expression. ("H+" indicates hormone presence, and "H−" indicates hormone absence.)
Figure 6:
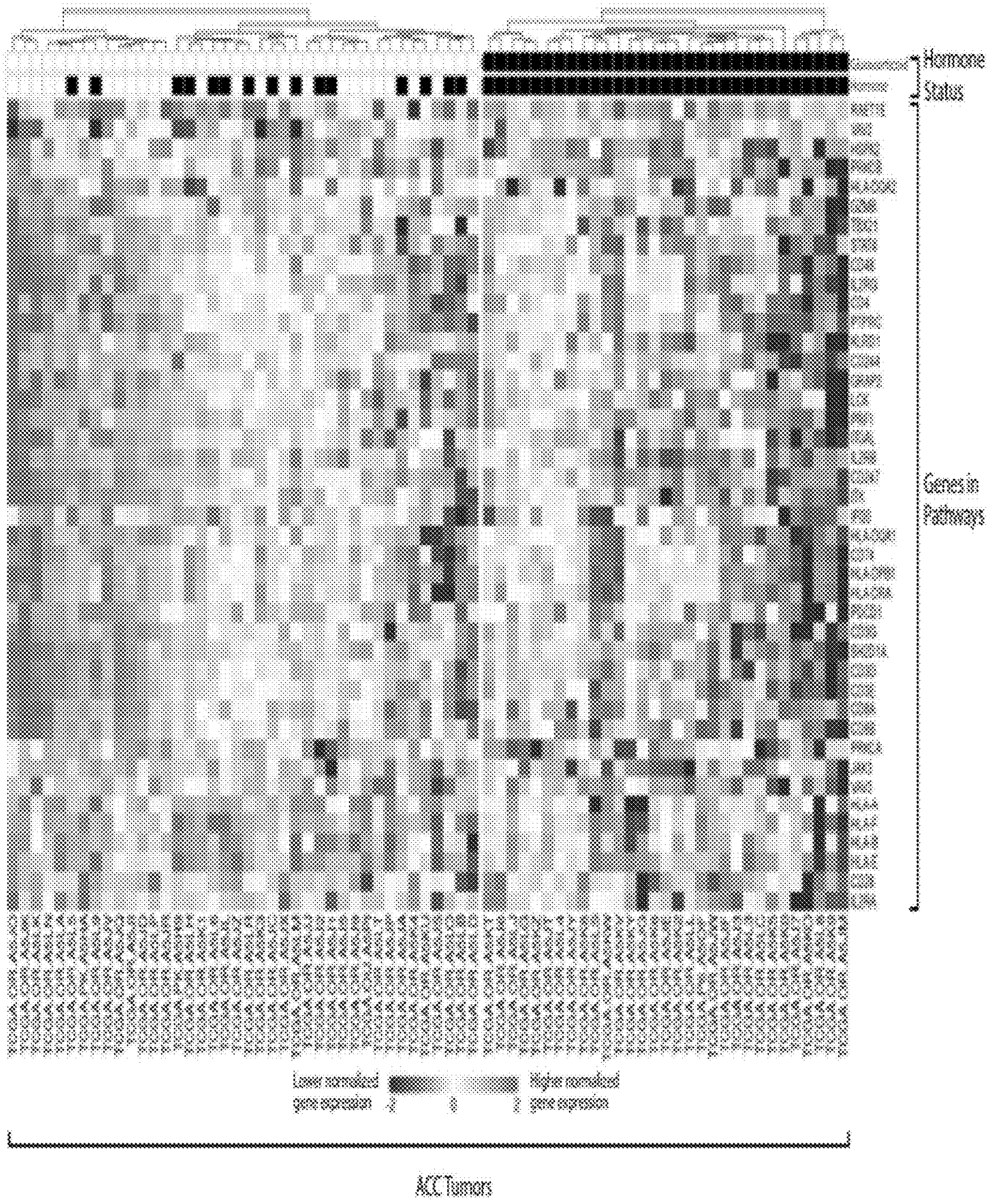
FIG. 6. Supervised Clustering of Normalized Gene Expression for the 2 KEGG Pathways Shown in FIG. 5. In GC+ cases (cluster on the right), lower expression of genes dominates these pathways (darker blue).

As illustrated in FIGS. 5 and 6, immune gene suppression is associated with GC Production. Unsupervised clustering of normalized gene expression for the T-cell receptor signaling and natural-killer-cell-mediated cytotoxicity KEGG pathways showed lower gene expression in GC+ cases (FIG. 5). Conversely, when clustering GC+ and GC− separately, GC+ cases trend toward lower expression in these two immune-related pathways (FIG. 6).

FIG. 5 illustrates unsupervised clustering of normalized gene expression for 2 KEGG Pathways. Pathways shown include T-cell receptor signaling and natural-killer-cell-mediated cytotoxicity. The top 2 rows indicate GC and general hormone status for each tumor (black: GC+/H+, white: GC−/H−), shades of blue/red (shown in grey scale) show normalized gene expression for each tumor, with darker blue corresponding to lower expression. When clustering by gene expression, GC+ cases appear toward the right of the figure, where many genes show lower expression.

FIG. 6. Supervised Clustering of Normalized Gene Expression for the 2 KEGG Pathways Shown in FIG. 5. In GC+ cases (cluster on the right), lower expression of genes dominates these pathways (darker blue).

Figure 7:
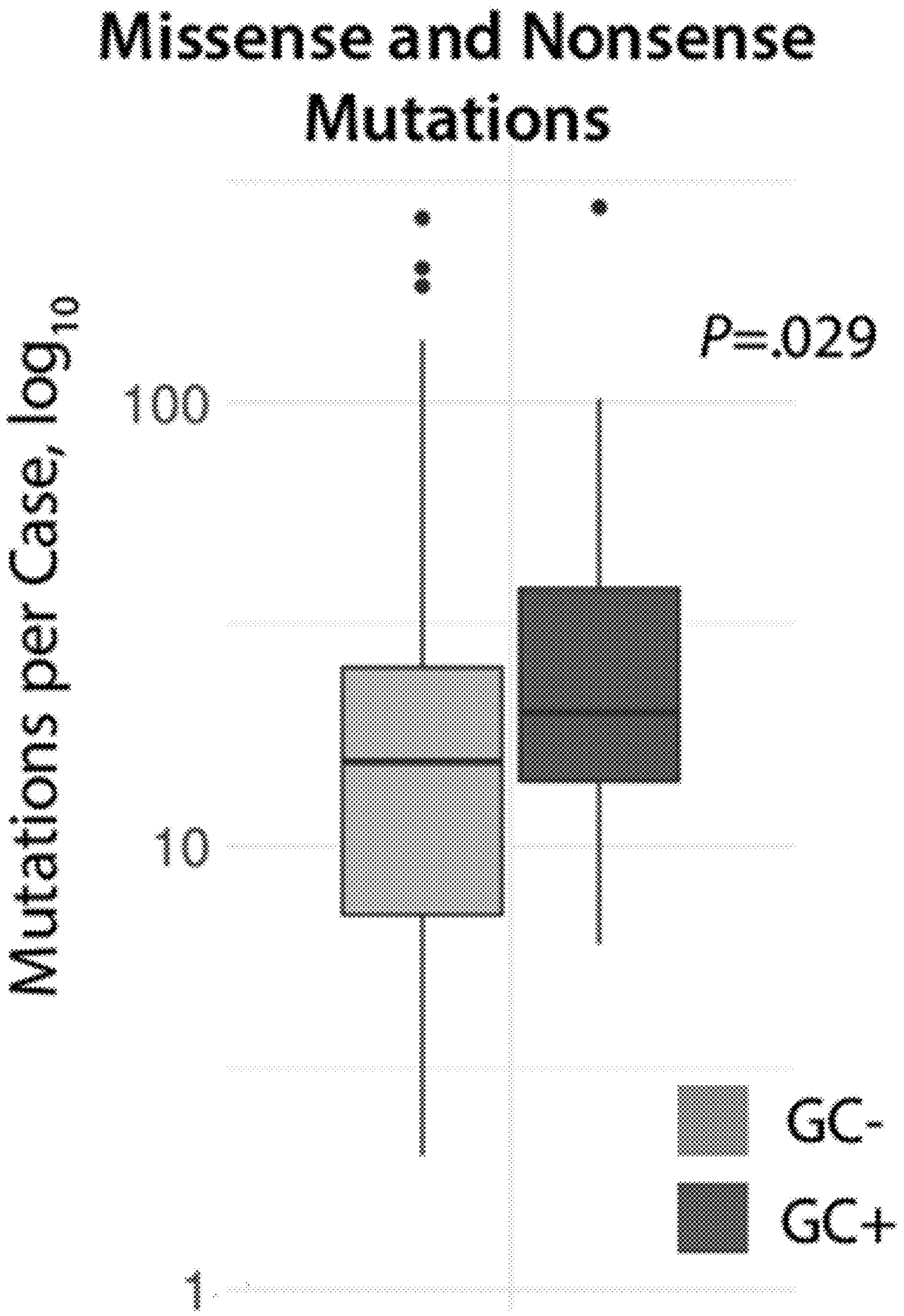
FIG. 7. Elevated Tumor Mutation Burden in GC+ ACC. In GC+ cases, more missense and nonsense mutations were observed compared to GC−.

FIG. 7. Elevated Tumor Mutation Burden in GC+ ACC. In GC+ cases, more missense and nonsense mutations were observed compared to GC− cases. (A case is an individual patient's tumor. "Mutations per case" are the total number of mutations identified in a single tumor.)

Figure 8:
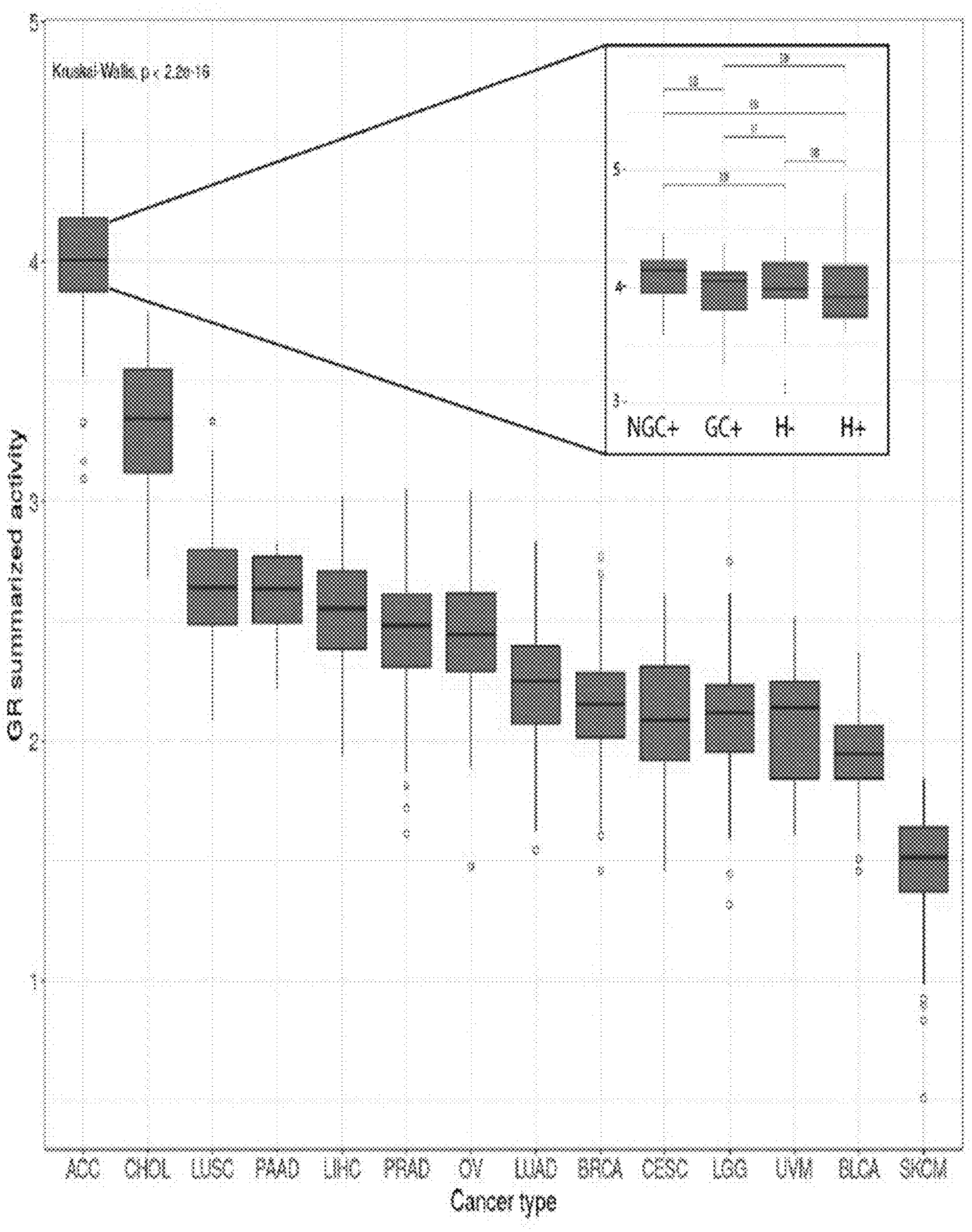
FIG. 8. GR Activity Score for Different Tumor Types and ACC Subsets. ACC exhibited high GR-driven gene activity relative to other tumors and independent of hormone status (see insert).

FIG. 8. GR Activity Score for Different Tumor Types and ACC Subsets. ACC exhibited high GR-driven gene activity relative to other tumors and independent of hormone status (see insert). GR activity is high in ACC, independent of hormone status. Tumor scoring using a published GR-driven gene signature determined from 74 GR activation-associated genes (West et al., 24(14):3433-3446 (2018)) confirmed that GR activity is high in ACC compared to other tumor types in the Cancer Genome Atlas (TCGA; FIG. 8). There was no difference between ACC cases with different hormone and GC status (insert in FIG. 8).

Figure 9:
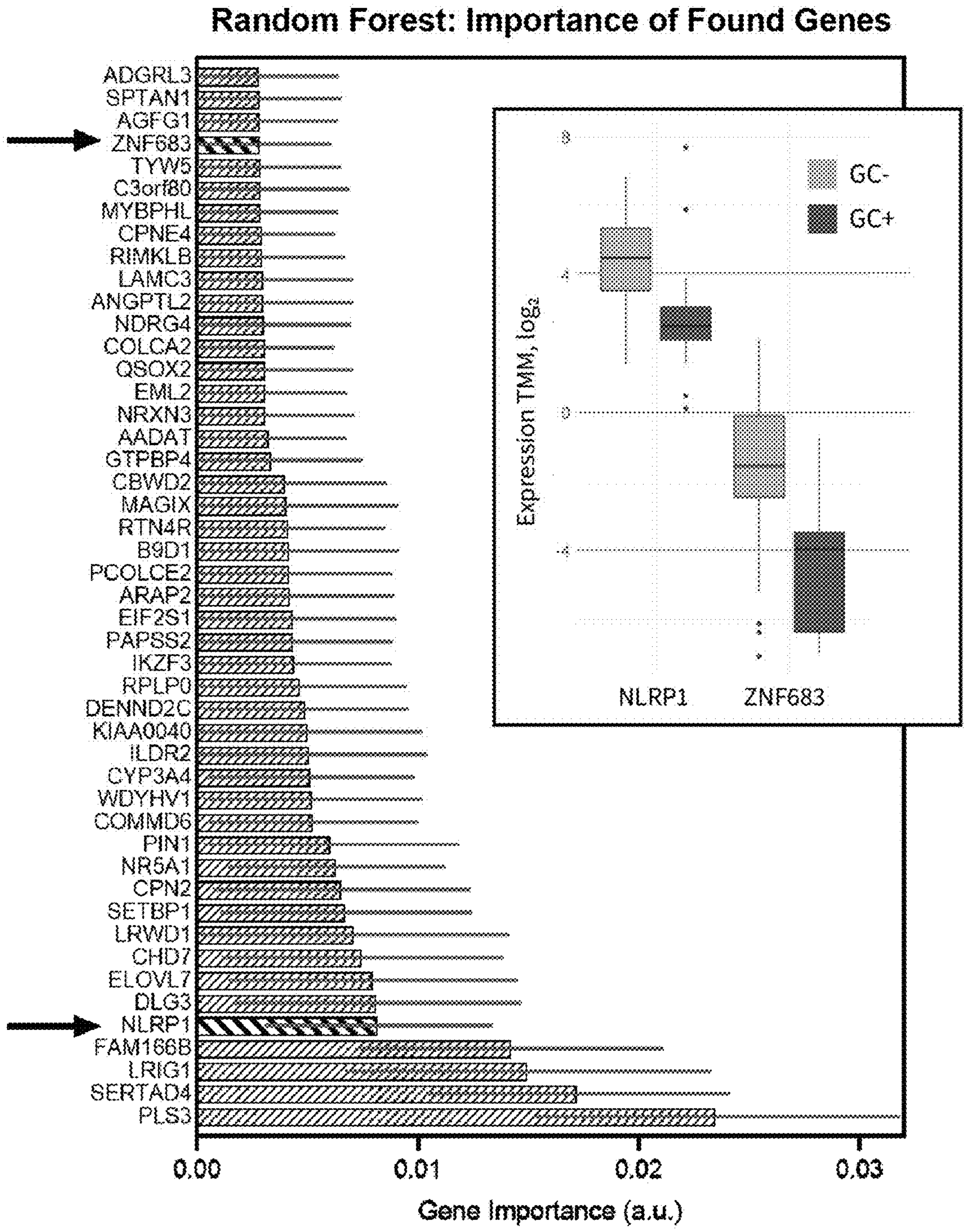
FIG. 9. Derivation of a Gene Signature that Distinguishes GC+/− ACC Cases Using Random Forest. NLRP1 and ZNF683 (highlighted) were identified as important components of the signature. Only signature genes above the threshold of 0.0028 are shown (where "a.u." indicates artificial units of importance for each gene).

FIG. 9. Gene signature can predict GC+-like tumor cases. FIG. 9 illustrates the results of derivation of a gene signature that distinguishes GC+/− ACC cases using Random Forest analysis. NLRP1 and ZNF683 (highlighted) were identified as important components of the signature. Only signature genes above the threshold of 0.0028 are shown. Random forest methods were used to derive a model that distinguishes GC+/− ACC cases with ROC AUC=0.87±0.09 (FIG. 9). The sensor component of the inflammasome (NLRP1) and a mediator of NK activation by IL-15 (ZNF683) were identified as important parts of this signature (insert in FIG. 9).

Figure 10A:
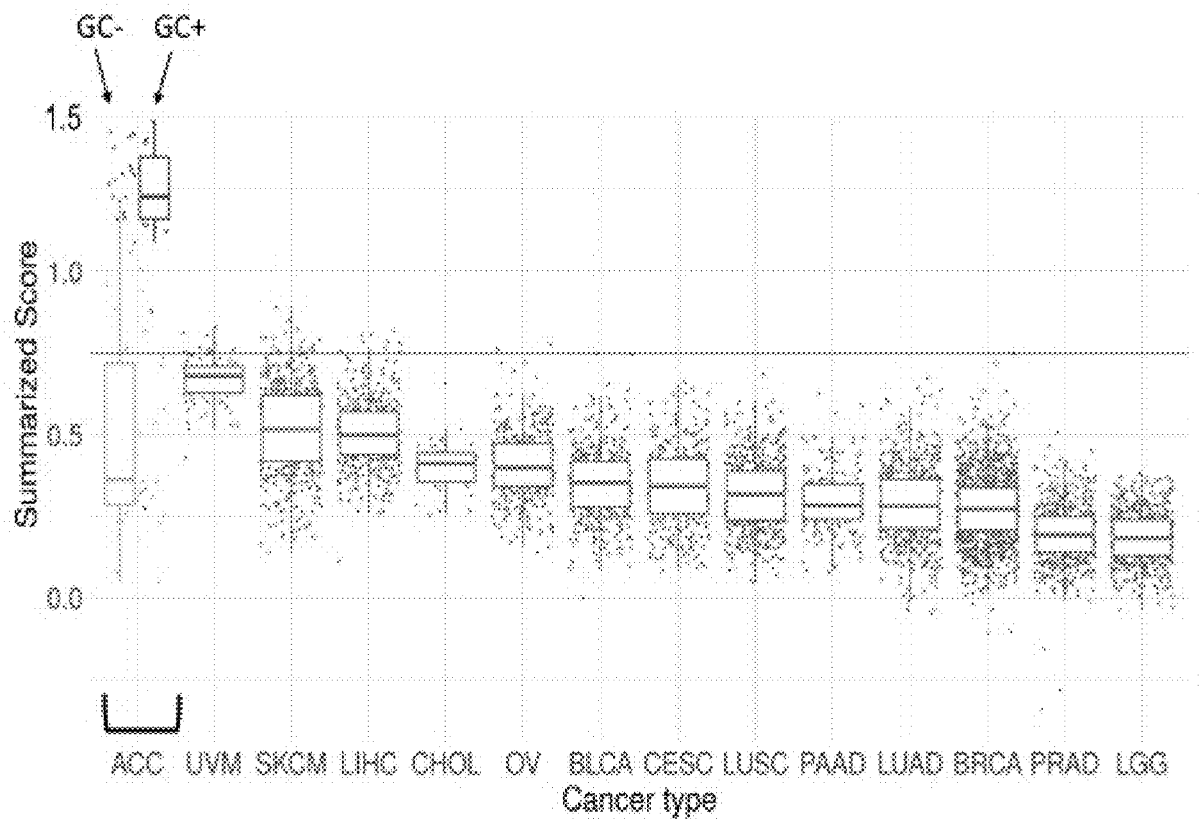
FIG. 10A. Application of the ACC Gene Signature to TCGA Tumors. Note that data from ACC tumors is shown in both left-most boxes (indicated by the bar above the label "ACC"). Data points from ACC patients without GC excess (GC−) and from patients with GC excess (GC+) are separately indicated by the labeled arrows above the corresponding boxes. Uveal (UVM) and skin cutaneous melanomas (SKCM) are predicted to have the highest frequency of tumors that resemble GC+ ACC.
Figure 10B:
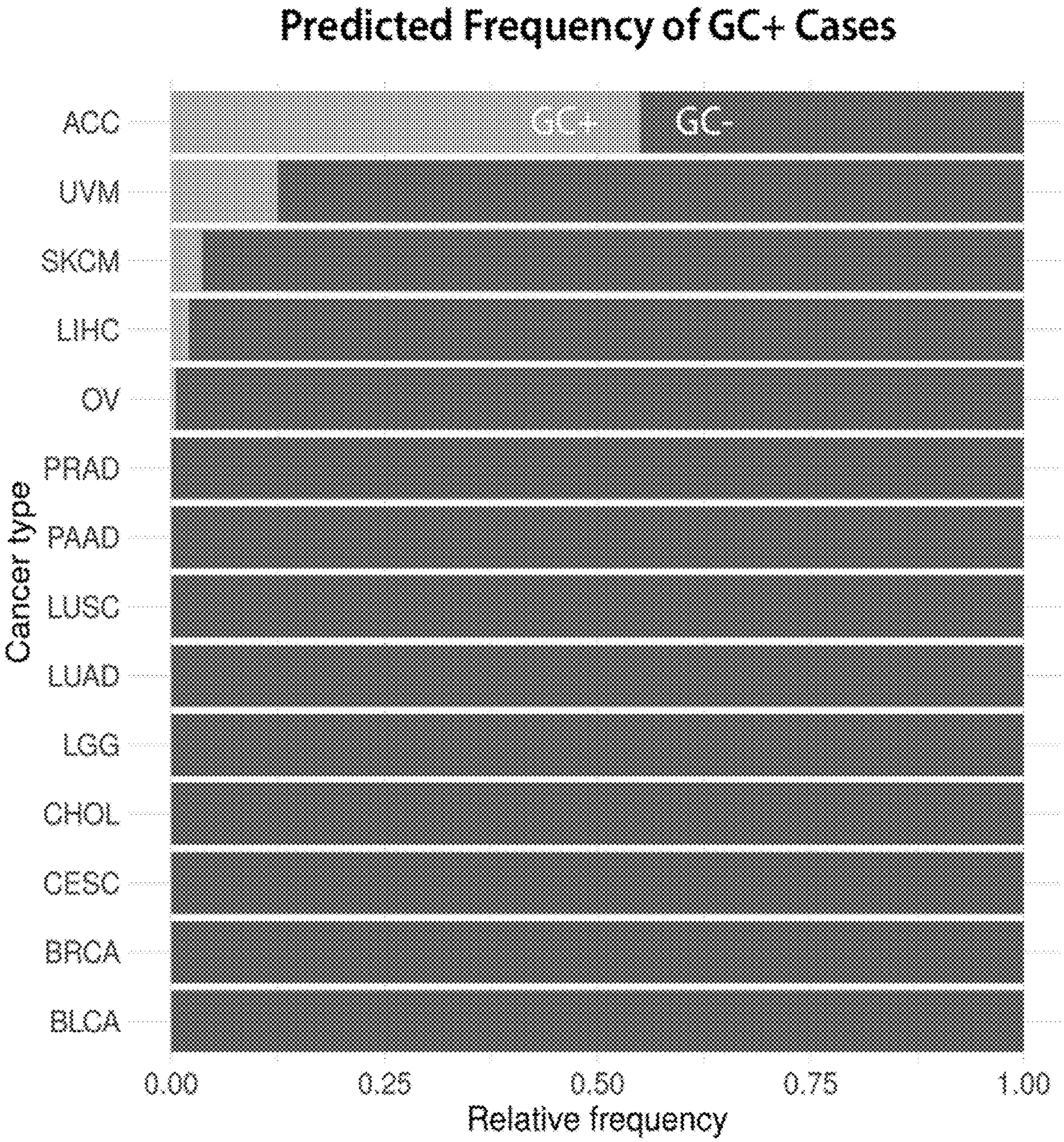
FIG. 10B. Predicted Frequency of Tumor Cases Resembling GC+ ACC. Uveal (UVM) and skin cutaneous melanomas (SKCM) are predicted to have the highest frequency of tumors that resemble GC+ ACC.

As shown in FIGS. 10A and 10B, the gene signature was then applied to other tumors types in TCGA to identify those with GC+-like transcriptional profiles. FIG. 10A shows the application of the ACC gene signature to TCGA tumors. Based on the known distribution of GC+/− cases in ACC, a cutoff score of 0.75 was derived to distinguish GC+/− tumors (horizontal line in FIG. 10A). According to this score, uveal (UVM) and cutaneous melanomas (SKCM) may have the highest frequency of cases similar to GC+ ACC (FIG. 10B). FIG. 10B shows the predicted frequency of tumor cases similar to GC+ ACC. Uveal (UVM) and skin cutaneous melanomas (SKCM) are predicted to have the highest frequency of tumors that resemble GC+ ACC.

Glucocorticoid excess (GC+) affects significantly more genes in ACC than other hormones. In GC+ ACC, expression of steroid synthesis genes was elevated while immune-related genes were suppressed. Normal adrenal cells express steroid synthesis genes but not immune-related genes. Steroid synthesis genes were hypomethylated in GC+ cases, while no difference in methylation between GC+ and GC− cases was found for immune genes. Furthermore, fewer infiltrating immune cells (T cells and NKT cells) were found in GC+ cases compared to GC−, suggesting that immune effects are due to changes in immune cell infiltrate rather than transcriptional changes. Tumor mutation burden was higher in GC+ ACC cases, which may be caused by the observed immune suppression or immune cell exclusion that may be related to higher tolerance of non-self-antigens in GC+ cases. A published GR activity score showed no difference between GC+ and GC− cases, which may be due to locally high concentrations of GC in the adrenal gland regardless of systemic GC levels. In contrast, immune infiltration into ACC tumors may be negatively affected by the exposure of lymph nodes to elevated GC activity. A newly derived gene signature predicts the highest frequency of GC+-like tumors in uveal and cutaneous melanomas. The observed reduced abundance of immune cells and immune-related transcripts in GC+ ACC provides insight into the mechanisms by which GC may limit response to immune system checkpoint inhibitor (ICI) therapy. GR antagonism may increase immune related transcripts or immune cell infiltration, thus promoting tumor immune response in GC+ ACC and other malignancies with elevated GC activity.

Example 4. Effects of Cortisol and Relacorilant on Natural Killer Cell Function In Vitro Given the pronounced differences in natural killer (NK) cells between GC+ and GC-ACC, the effects of cortisol were assessed on human NK cells in vitro. Cortisol suppressed (and relacorilant restored) NK cell activation, proliferation, and direct tumor cell killing. Reduced abundance of NK cells, and other immune cells, in GC+ ACC provides insight into the mechanisms by which GC may limit response to ICI therapy. GR antagonism may increase the abundance and function of NK cells and other immune cells in the tumor, thus promoting tumor immune response in GC+ ACC and other malignancies with elevated GC activity. This hypothesis will be tested in a Phase 1 trial of relacorilant+ICI.

Effects of Cortisol and Relacorilant on NK Cell Function In Vitro

Figure 11A:
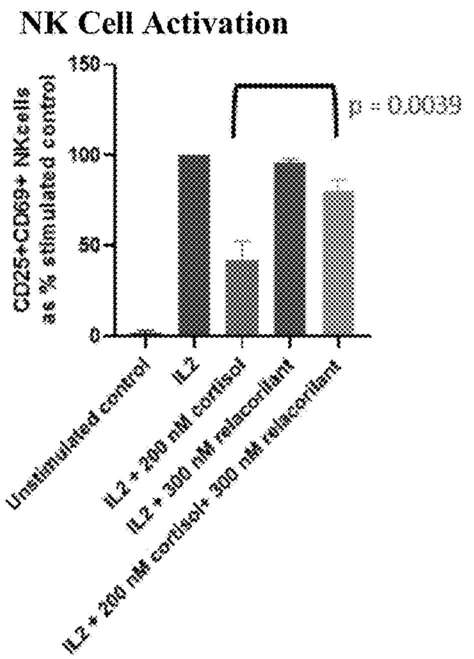
FIG. 11A. Effects of stimulation with IL-2, cortisol, and/or relacorilant on isolated human NK cells in vitro. Addition of relacorilant significantly improved natural killer (NK) cell activation in response to IL-2.
Figure 11B:
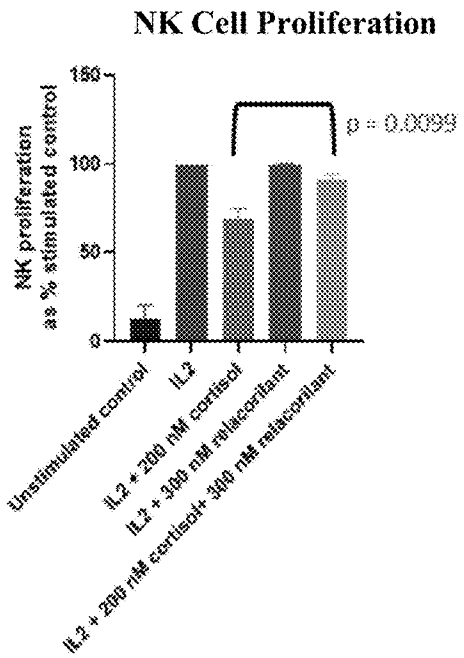
FIG. 11B. Effects of stimulation with IL-2, cortisol, and/or relacorilant on isolated human NK cells in vitro. Addition of relacorilant significantly improved NK cell proliferation in response to IL-2.
Figure 12A:
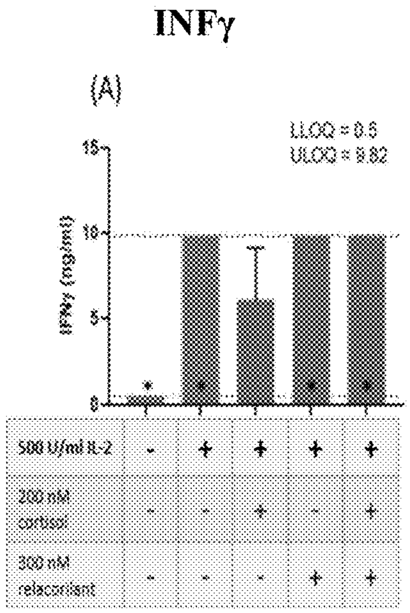
FIG. 12A. Effects of stimulation with IL-2, cortisol, and/or relacorilant on isolated human NK cells cytokine secretion and gene expression. Addition of relacorilant improved interferon γ (IFNγ) secretion relative to NK cells treated with cortisol alone.
Figure 12B:
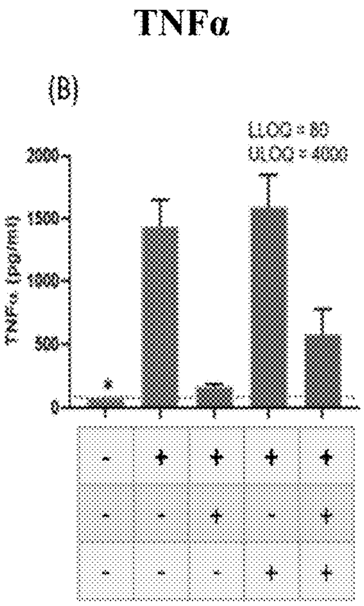
FIG. 12B. Effects of stimulation with IL-2, cortisol, and/or relacorilant on isolated human NK cells cytokine secretion and gene expression. Addition of relacorilant improved tumor necrosis factor (TNFα) secretion relative to NK cells treated with cortisol alone.
Figure 12C:
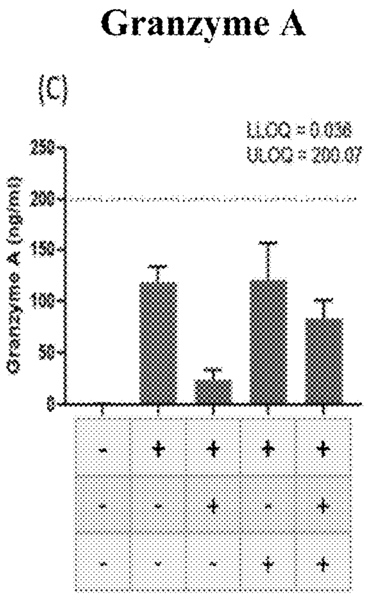
FIG. 12C. Effects of stimulation with IL-2, cortisol, and/or relacorilant on isolated human NK cells cytokine secretion and gene expression. Addition of relacorilant improved Granzyme A secretion relative to NK cells treated with cortisol alone.
Figure 12D:
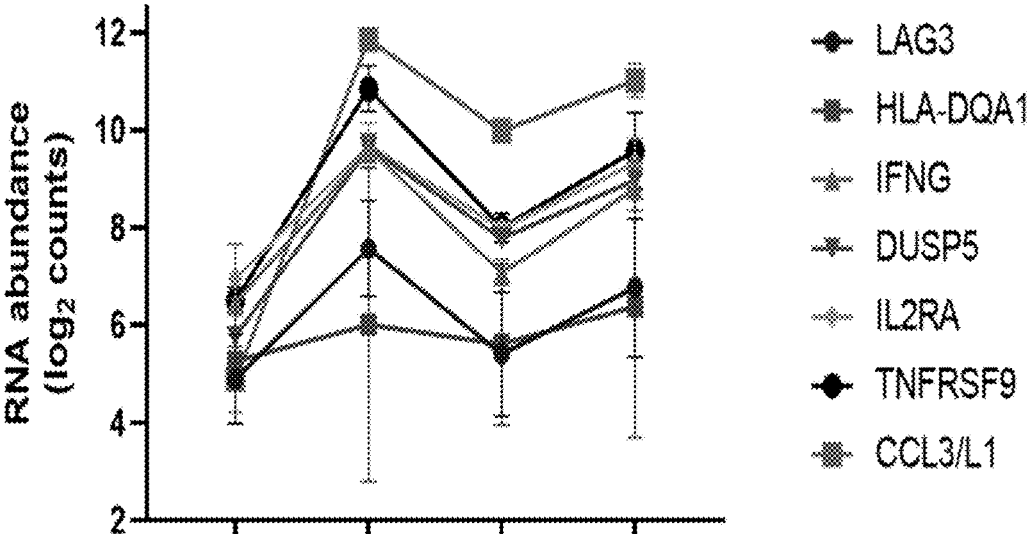
FIG. 12D. Effects of stimulation with IL-2, cortisol, and/or relacorilant on isolated human NK cells gene expression. Transcription of IFNG (which codes for IFNγ) is also improved by relacorilant along with other key regulators of NK activity including LAG3 and the IL2RA (which codes for the interleukin 2 (IL2) receptor).

Given the prominent suppression of NK related genes in GC+ cases, the direct effects of GR modulation of human NK cells were assessed. NK cells were isolated from healthy donors and stimulated with IL-2. Activation (abundance of CD25+CD69+ cells) was increased by stimulation, suppressed by cortisol, and restored by relacorilant (Mann-Whitney p=0.0039) (FIG. 11A). Proliferation of NK cells was also increased by stimulation, suppressed by cortisol, and restored by relacorilant (Mann-Whitney p=0.0099) (FIG. 11B). Cytokine secretion (both transcript and secreted protein) was also increased by stimulation, suppressed by cortisol, and restored by relacorilant (FIGS. 12A-12D). Genes that were significantly induced by stimulation, suppressed by cortisol, and restored by relacorilant included key NK activation genes including the IL2 receptor and the activator LAG3. (FIG. 12D). These data provide experimental confirmation of the observed effects of GC on NK cell populations in ACC tumors.

Figure 13A:
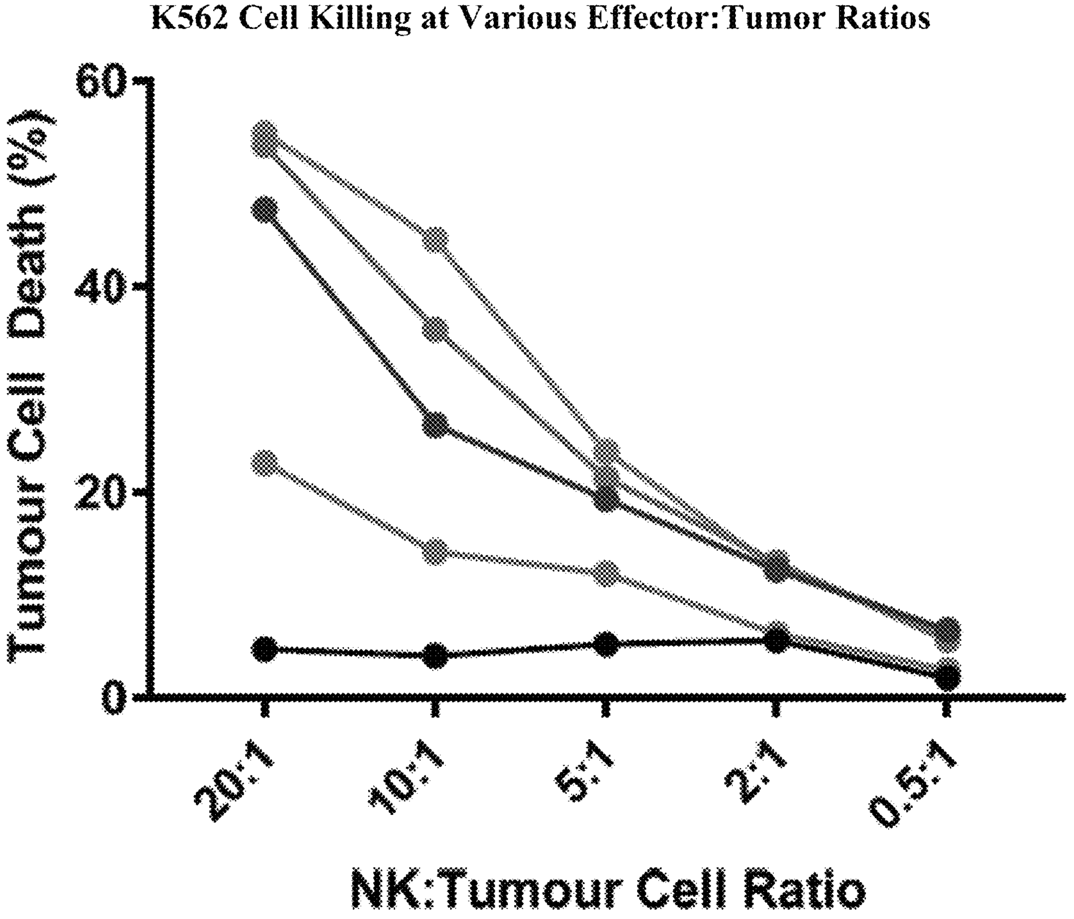
FIG. 13A. Glucocorticoids suppress tumor cell killing by human NK cells in vitro. K562 cell killing at various ratios of effector:tumor cells under the treatment conditions listed in the legend. This is counteracted by relacorilant.
Figure 13B:
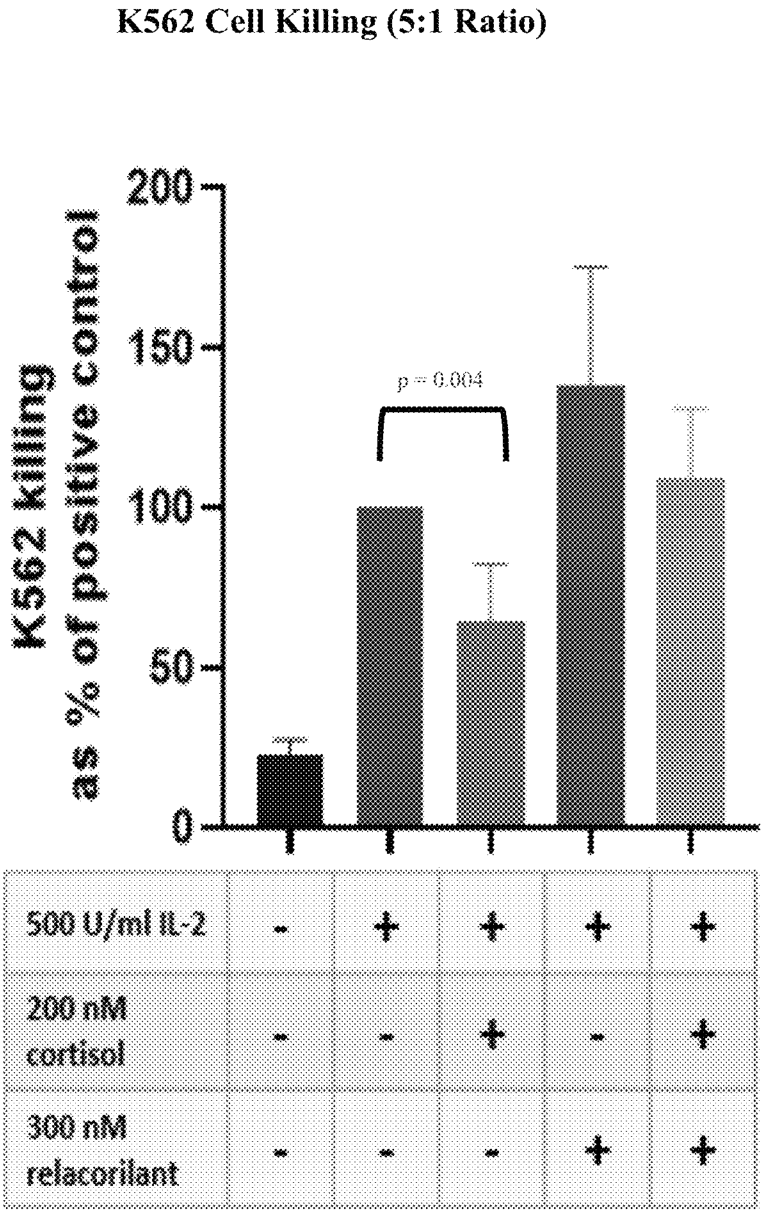
FIG. 13B. Glucocorticoids suppress tumor cell killing by human NK cells in vitro. At the 5:1 effector:tumor cell ratio, the significant decrease in tumor cell killing in the presence of cortisol is counteracted by relacorilant.

Activation, proliferation, and cytokine secretion are all indicative of a functional change in NK cells mediated by cortisol and relacorilant. To determine if this functional change also affected target cell killing, NK cells were incubated with K562 tumor cells. At various NK:tumor cell ratios, cortisol suppressed tumor cell killing and relacorilant restored it (FIG. 13A). There was a significant improvement in NK cell tumor killing when relacorilant was added to the NK cells at the 5:1 ratio (Mann-Whitney p=0.004) (FIG. 13B). Thus, glucocorticoids suppress tumor cell killing by human NK cells in vitro.

Cortisol is a potent transcriptional regulator and mediator of immune cell function. Assessing the effects of systemic cortisol activity is challenging because cortisol's diurnal and ultradian variations limit the interpretability of any single cortisol assessment. ACC multi-omics data provides a unique scenario in which rich multi-omics data are paired with clinical assessment of cortisol excess. This exaggerated cortisol physiology was investigated both to better understand ACC and to glean insights into possible sub-clinical manifestations of cortisol activity in other tumor types.

Significant differences in 858 genes were observed between ACC cases with or without GC excess. Fewer genes were significantly different across other comparisons, such as cases + vs − for any steroid hormone. Genes involved in steroid synthesis were, unsurprisingly, high in cases with GC excess. Promoter hypomethylation was observed for steroid synthesis genes. In contrast, reduced expression of immune genes in GC+ cases was likely a consequence of poor infiltration of immune cells into GC+ tumors. Assessment of GR activity (via a published gene signature; see West et al., Clin Cancer Res, 2018. 24(14): p. 3433-3446) suggested that the intratumor GR activity is similar in ACC cases with or without GC excess. This may be drive by high cortisol levels with the adrenal gland independent of systemic cortisol levels. Thus the differences in immune infiltration may be due to the systemic effects of GC, including effects on primary and secondary lymphoid organs throughout the body. Effects of GC on lymphoid organs may also be related to the increased TMB observed in GC+ ACC cases, as high GC may increase tolerance toward neoantigens.

Using the GC+ vs GC− cases, a gene signature was discovered than can distinguish the two. This gene signature could be useful in future efforts to diagnose GC excess from a tumor biopsy or resection. When non-ACC tumors were scored for this signature, uveal and cutaneous melanomas exhibited the most frequent (albeit still rare) cases that resembled the transcriptional signature of GC+ ACC. This supports previous reports of local cortisol production in the skin (see Vekulic et al., and Tissue Injury. J Biological Chemistry, 2011. 286(12) pp. 10265-10275). Such tumors would provide a rationale choice for assessment of immune effects of GR antagonism outside ACC.

Suppression of NK cells was prominent in the GC+ ACC multi-omics data. NK activation genes were significantly lower in GC+ cases, and the NK activation gene ZNF683 was among the most important genes in distinguishing GC+ from GC− cases. Functional studies with human NK cells, cortisol, and the GR modulator relacorilant confirmed that GR is a key regulator of NK function. Cortisol suppressed NK proliferation, upregulation of cell surface markers of activation, tumor cell killing, IFNγ secretion, and IFNγ transcription. It also suppressed secretion of other effector cytokines and expression of the IL-2 receptor (il2ra). These observations corroborate the decrease in NK activation genes observed in GC+ ACC. Cortisol suppressed, and relacorilant promoted, the expression of LAG3 (CD223, lag3) and 4-1BB (CD137 tnfrsf9), both targets of experimental agonists intended to improve the anti-tumor immune response. Expression of chemokine ligand 3-like 1 (ccl3l1), a chemokine that attracts lymphocytes, was also suppressed by cortisol in stimulated NK cells, which could explain the reduced T-cell infiltrate into the GC+ ACC as well. The observed reduced abundance of immune-related transcripts in GC+ ACC provides insight into the mechanisms by which GC may limit response to ICI therapy.

Adrenal cancer is a grievous disease in which patients face challenges both in tumor and hormone management. ACC patients with cortisol excess experience Cushing's Syndrome, a condition that describes systemic excess cortisol from adrenal, pituitary, or ectopic origin. Cushing's syndrome itself can lead to death via vascular events, cardiovascular events, or infections in these patients (see Yaneva M., et al., European J Endocrinology 2013, 169 621-627). The GR modulator Korylm™ (mifepristone) is approved for treatment of the symptoms of cortisol excess. These data go a step further and suggest that selective GR modulation with relacorilant can relieve the immune suppression caused by systemic cortisol. Thus, selective GR antagonism could both promote antitumor efficacy of other immune modulators, such as immune checkpoint inhibitors or more experimental NK-targeting agents, and reduce the dangerous sequalae of cortisol excess. This hypothesis is being tested directly in a current phase I study or relacorilant+pembrolizumab in ACC patient with GC excess.

The effects of GC excess on NK cells were particularly pronounced, and direct assessment of cortisol effects on NK cells in vitro confirmed potent and broad suppressive activity. Further, relacorilant could reverse the effects of cortisol and restore NK cell activation, proliferation, and target cell killing. Accordingly, these it is believed that treatment of adrenocortical carcinoma patients suffering from excess cortisol (GC+ ACC) by combined administration of a GR modulator, such as relacorilant, and an immune checkpoint inhibitor (ICI), provide efficacious and improved treatment as compared to treatment with an ICI alone.

All patents, patent publications, publications, and patent applications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of treating a patient suffering from adrenocortical carcinoma (ACC), said patient having an ACC tumor or tumors, the amount of said ACC tumor or tumors being the ACC tumor load of the patient, the patient having cortisol excess, and having lower expression of the gene ZNF683 in said ACC tumor or tumors as compared to ZNF683 expression in ACC tumors in patients who suffer from ACC without cortisol excess, the method comprising:

Identifying a patient a) suffering from adrenocortical carcinoma (ACC), b) suffering from cortisol excess, and c) having lower expression of the gene ZNF683 as compared to ZNF683 expression in patients without cortisol excess who suffer from ACC;

administering to said patient a combination treatment comprising administration of 1) a selective glucocorticoid receptor modulator (SGRM), wherein said SGRM is a heteroaryl-ketone fused azadecalin compound having the formula:

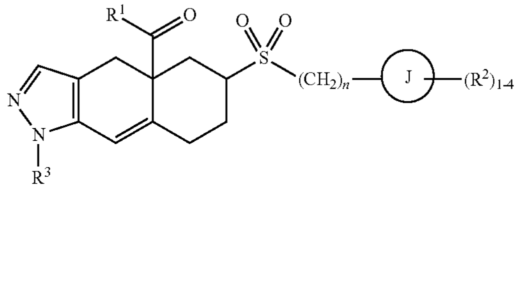

wherein $R^1$ is a heteroaryl ring having from 5 to 6 ring members and from 1 to 4 heteroatoms each independently selected from the group consisting of N, O and S, optionally substituted with 1 to 4 $R^{1a}$ groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;

alternatively, two $R^2$ groups linked to the same carbon are combined to form an oxo group (=O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$;

each $R^{2d}$ is independently selected from the group consisting of hydrogen and $C_{1-6}$ alkyl, or two $R^{2d}$ groups attached to the same ring atom are combined to form (=O);

$R^3$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

or salts and isomers thereof, and

2) An antibody checkpoint inhibitor to said identified patient;

thereby achieving a better treatment outcome from said identified patient than would be achieved by treatment with an antibody checkpoint inhibitor alone, wherein said treatment outcome is selected from a) reduction in said patient's ACC tumor load, b) restoration of T-cell and natural killer (NK) cell signaling pathways in the patient, c) increased T-cell and NK cell infiltration into the ACC in the patient, and d) reduced neutrophil infiltration into the ACC in the patient.

2. The method of claim 1, wherein the antibody checkpoint inhibitor is selected from an antibody effective against PD-1, an antibody effective against CTLA-4, an antibody effective against PD-L1, and an antibody effective against PD-L2.

3. The method of claim 1, wherein the method further comprises administering a taxane chemotherapeutic agent.

4. The method of claim 3, wherein said taxane chemotherapeutic agent is nab-paclitaxel.

5. The method of claim 1, wherein said SGRM is the heteroaryl-ketone fused azadecalin compound (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl) (4-(trifluoromethyl) pyridin-2-yl) methanone, termed relacorilant, which has the following structure:

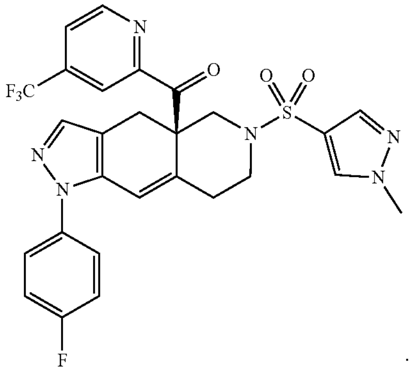 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

.

6. The method of claim 1, wherein the antibody checkpoint inhibitor is selected from an antibody effective against PD-1, an antibody effective against CTLA-4, and an antibody effective against PD-L1.

7. The method of claim 1, wherein the SGRM is the heteroaryl-ketone fused azadecalin compound (R)-(1-(4-fluorophenyl)-6-((4-(trifluoromethyl)phenyl) sulfonyl)-4,4a, 5,6,7,8-hexahydro-1-H-pyrazolo P,4-g]isoquinolin-4a-yl) (pyridin-2-yl) methanone (termed "CORT113176"), which has the following structure:

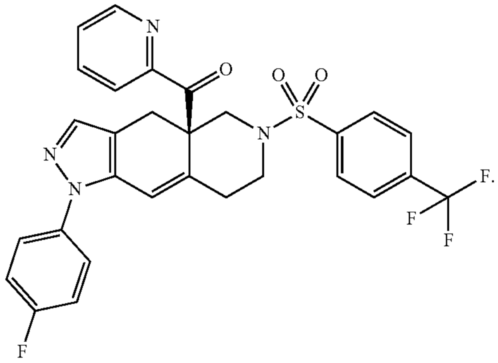 [SMILES: O=C(c1ccccn1)[C@]12Cc3cnn(-c4ccc(F)cc4)c3C=C1CCN(S(=O)(=O)c1ccc(C(F)(F)F)cc1)C2]

* * * * *